United States Patent [19]

Oida et al.

[11] Patent Number: 5,489,606
[45] Date of Patent: Feb. 6, 1996

[54] ANTI-FUNGAL TRIAZOLE DERIVATIVES, THEIR USES

[75] Inventors: Sadao Oida; Takeo Miyaoka; Yawara Tajima; Toshiyuki Konosu; Noriko Takeda; Hiroshi Yasuda, all of Tokyo, Japan

[73] Assignee: Sankyo Company, Limited, Tokyo, Japan

[21] Appl. No.: 316,082

[22] Filed: Sep. 30, 1994

Related U.S. Application Data

[62] Division of Ser. No. 24,827, Mar. 1, 1993, Pat. No. 5,393,769, which is a continuation of Ser. No. 749;562, Aug. 26, 1991, abandoned.

[30]   Foreign Application Priority Data

Aug. 28, 1990 [JP] Japan ..................... 2-225762

[51] Int. Cl.$^6$ ....................... A01N 43/653; C07D 249/08
[52] U.S. Cl. .......................... 514/383; 548/268.6
[58] Field of Search ..................... 514/383; 548/268.6

[56]         References Cited

U.S. PATENT DOCUMENTS 5,004,494   4/1991   Sugauanam et al. ............... 548/268.6
5,177,094   1/1993   Itoh et al. ............................. 548/268.6
5,405,861   4/1995   Itoh et al. ............................. 548/268.6

*Primary Examiner*—Patricia L. Morris
*Attorney, Agent, or Firm*—Frishauf, Holtz, Goodman, Langer & Chick

[57]         ABSTRACT

Compounds of formula (I):

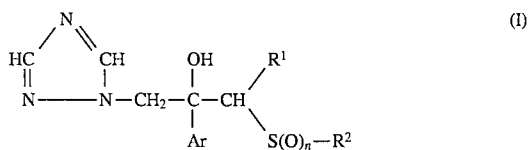

in which: Ar is optionally substituted phenyl; is $R^1$ is alkyl; $R^2$ is substituted alkyl, substituted cycloalkyl $R^2$ or optionally substituted heterocyclic; and n is 0, 1 or 2; and pharmaceutically acceptable salts and esters thereof have valuable anti-fungal properties and can be used for pharmaceutical and veterinary treatment. Methods of preparing these compounds are also provided.

9 Claims, No Drawings

ANTI-FUNGAL TRIAZOLE DERIVATIVES, THEIR USES

This is a division of application Ser. No. 08/024,827 filed Mar. 1, 1993, now U.S. Pat. No. 5,393,769 issued Feb. 28, 1985 which is a continuation of application Ser. No. 07/749,562 filed Aug. 26, 1991 (abandoned).

BACKGROUND TO THE INVENTION

The present invention relates to a series of new 1-(triazol-1-yl)-2-phenyl-3-(substituted thio, sulfinyl or sulfonyl)-2-alkanol derivatives which have pharmaceutical and veterinary anti-fungal activity, and which can thus be used for the treatment and prophylaxis of fungal infections, especially internal fungal infections, in humans and other animals. The invention also provides processes for preparing these compounds as well as methods and compositions using them.

A series of 1-(triazol-1-yl)-2-phenyl-3-(substituted thio, sulfinyl or sulfonyl)-2-alkanol derivatives is disclosed in European Patent Publication No. 178 533, and these are said to have anti-fungal activity. The prior compounds differ from those of the present invention in that the compounds of the present invention have certain specific substituents on the thio, sulfinyl or sulfonyl group. As a result the compounds of the present invention have significantly better anti-fungal activity than do the prior art compounds.

BRIEF SUMMARY OF INVENTION

The compounds of the present invention are thus those compounds of formula (I):

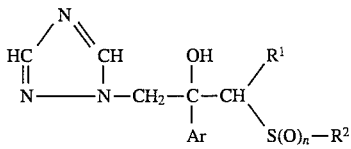

in which:
Ar represents an unsubstituted phenyl group or a substituted phenyl group which is substituted by at least one substituent selected from the group consisting of halogen atoms and trifluoromethyl groups;
$R^1$ represents an alkyl group having from 1 to 4 carbon atoms;
$R^2$ represents:
  a substituted alkyl group having from 1 to 5 carbon atoms and substituted by at least one substituent selected from the group consisting of substituents (a), defined below;
  a substituted cycloalkyl group having from 3 to 6 ring carbon atoms and substituted by at least one substituent selected from the group consisting of substituents (b), defined below; or
  a heterocyclic group having from 3 to 6 ring atoms, of which from 1 to 3 are hetero-atoms selected from the group consisting of nitrogen, oxygen and sulfur heteroatoms, said group being unsubstituted or being substituted by at least one substituent selected from the group consisting of substituents (c), defined below; and
n is 0, 1 or 2;
substituents (a):
  substituted cycloalkyl groups having from 3 to 6 ring carbon atoms and substituted by at least one substituent selected from the group consisting of substituents (b), defined below;
  heterocyclic groups having from 3 to 6 ring atoms, of which from 1 to 3 are hetero-atoms selected from the group consisting of nitrogen, oxygen and sulfur heteroatoms, said group being unsubstituted or being substituted by at least one substituent selected from the group consisting of substituents (c), defined below;
  groups of formula —$OR^3$, where $R^3$ represents a hydrogen atom or an alkyl group having from 1 to 4 carbon atoms;
  groups of formula =$NOR^4$, where $R^4$ represents a hydrogen atom or an alkyl group having from 1 to 4 carbon atoms;
  groups of formula —$NHOR^5$, where $R^5$ represents a hydrogen atom or an alkyl group having from 1 to 4 carbon atoms;
  groups of formula —$NR^6R^7$, where $R^6$ and $R^7$ are the same or different and each represents a hydrogen atom or an alkyl group having from 1 to 4 carbon atoms;
  groups of formula —$NHCOR^8$, where $R^8$ represents a hydrogen atom or an alkyl group having from 1 to 4 carbon atoms;
  carboxy groups;
  groups of formula —$CONR^{10}R^{11}$, where $R^{10}$ and $R^{11}$ are the same or different and each represents a hydrogen atom or an alkyl group having from 1 to 4 carbon atoms;
  groups of formula —$S(O)_mR^{12}$, were $R^{12}$ represents a hydrogen atom or an alkyl group having from 1 to 4 carbon atoms and m is 0, 1 or 2; and
  formyl, cyano and nitro groups;
substituents (b):
  groups of formula —$OR^3$, where $R^3$ is as defined above;
  groups of formula =$NOR^4$, where $R^4$ is as defined above;
  groups of formula —$NHOR^5$, where $R^5$ is as defined above;
  groups of formula —$NR^6R^7$, where $R^6$ and $R^7$ are the same or different and each is as defined above;
  groups of formula —$NHCOR^8$, where $R^8$ is as defined above;
  carboxy groups;
  groups of formula —$CONR^{10}R^{11}$, where $R^{10}$ and $R^{11}$ are the same or different and each is as defined above;
  groups of formula —$S(O)_mR^{12}$, where $R^{12}$ and m are as defined above;
  oxygen atoms (to form an oxo group); and
  formyl, cyano, hydroxymethyl and nitro groups;
substituents (c):
  alkyl groups having from 1 to 4 carbon atoms;
  groups of formula —$OR^3$, where $R^3$ is as defined above;
  groups of formula —$NR^6R^7$, where $R^6$ and $R^7$ are the same or different and each is as defined above;
  carboxy groups;
  groups of formula —$CONR^{10}R^{11}$ where $R^{10}$ and $R^{11}$ are the same or different and each is as defined above;
  groups of formula —$S(O)_mR^{12}$, where $R^{12}$ and m are as defined above;
  oxygen atoms (to form an oxo group); and
  formyl and hydroxymethyl groups;
and pharmaceutically acceptable salts and esters thereof.

The invention also provides a pharmaceutical or veterinary composition for the treatment or prophylaxis of fungal infections, which comprises an anti-fungal agent in admixture with a pharmaceutically or veterinarily acceptable carrier or diluent, wherein the anti-fungal agent is at least one compound selected from the group consisting of compounds of formula (I) and pharmaceutically acceptable salts and esters thereof.

The invention also provides a method for the treatment or prophylaxis of fungal infections in an animal, e.g. a mammal, which may be human, which method comprises administering to said animal an anti-fungal agent, wherein the anti-fungal agent is at least one compound selected from the group consisting of compounds of formula (I) and pharmaceutically acceptable salts and esters thereof.

DETAILED DESCRIPTION OF INVENTION

In the compounds of the present invention, where Ar represents a substituted phenyl group, the substituents are selected from the group consisting of halogen atoms and trifluoromethyl groups. There is no particular restriction on the number of substituents, except that imposed by the number of substitutable positions, i.e. the maximum number is 5; in general, however, from 1 to 3 substitutents are preferred, and, when there are 2 or 3 substituents, these may be the same or different. Where there is a single substituent only, this is preferably on the 2- or 4- position of the phenyl group, more preferably the 4-position. Where there are 2 substituents, these are preferably at the 2- and 4-positions. Where there are 3 substituents, these are preferably at the 2-, 4- and 6- positions. However, we prefer those compounds with 1 or 2 substituents, more preferably at the 4- and the 2,4- positions, respectively.

Where the substituent on the phenyl group represented by Ar is a halogen atom, this may be a fluorine, chlorine, bromine or iodine atom, more preferably a fluorine or chlorine atom. The preferred groups to be represented by Ar are the 2,4-dichlorophenyl, 2,4-difluorophenyl, 4-chlorophenyl, 2-chloro-4-fluorophenyl, 2-fluoro-4-chlorophenyl, 2-fluoro-4-(trifluoromethyl)phenyl and 4-(trifluoromethyl)phenyl groups, more preferably the 2,4-dichlorophenyl, 2,4-difluorophenyl, 4-chlorophenyl and 2-fluoro-4-chlorophenyl groups, and most preferably the 2,4-difluorophenyl and 4-chlorophenyl groups.

$R^1$ represents a lower alkyl group, which may be a straight or branched chain alkyl group having from 1 to 4 carbon atoms, and examples include the methyl, ethyl, propyl, isopropyl, butyl, isobutyl, sec-butyl and t-butyl groups. Of these, we prefer the methyl, ethyl and propyl groups, more preferably the methyl and ethyl groups and most preferably the methyl group.

Where $R^2$ represents an alkyl group, this may be a straight or branched chain alkyl group having from 1 to 5 carbon atoms; this group must be substituted by at least one, and preferably from 1 to 3, of substituents (a), as defined above. We most prefer only one such substituent. Examples of the alkyl groups include the methyl, ethyl, propyl, isopropyl, butyl, isobutyl, sec-butyl, t-butyl, pentyl, isopentyl and t-pentyl groups, of which the methyl, ethyl and propyl groups are preferred. In general, from 1 to 4 (more preferably 1 to 3) carbon atoms are preferred in the alkyl group, except where the substituent is a group of formula $=NOR^4$, when from 2 to 5 (more preferably 2 or 3) carbon atoms are preferred.

The substituents on the alkyl groups represented by $R^2$ are selected from the group consisting of substituents (a), defined above, whilst those on the cycloalkyl and heterocyclic groups are selected from the group consisting of substituents (b) and (c), repectively, in which each of $R^3$, $R^4$, $R^5$, $R^6$, $R^7$, $R^8$, $R^{10}$, $R^{11}$ and $R^{12}$ is independently selected from the group consisting of hydrogen atoms and alkyl groups having from 1 to 5 carbon atoms. In the case where substituent (a), (b) or (c) represents a carboxy group, this may be esterified to form a group of formula —$COOR^9$, where $R^9$ represents an alkyl group having from 1 to 5 carbon atoms. In all cases, the alkyl group may be a straight or branched chain alkyl group having from 1 to 5 carbon atoms, and examples of the alkyl groups include the methyl, ethyl, propyl, isopropyl, butyl, isobutyl, sec-butyl, t-butyl, pentyl, isopentyl and t-pentyl groups, of which the methyl, ethyl and propyl groups are preferred.

Where $R^2$ or substituent (a) represents a cycloalkyl group, this has from 3 to 6 carbon atoms, and examples of such groups include the cyclopropyl, cyclobutyl, cyclopentyl and cyclohexyl groups, of which the cyclopropyl and cyclobutyl groups are preferred. Such groups are substituted by at least one of substituents (b), defined above.

Where $R^2$ or substituent (a) represents a heterocyclic group, this has from 3 to 6 ring atoms, more preferably 5 or 6 ring atoms, of which from one to three (more preferably two) are hetero-atoms selected from the group consisting of nitrogen, oxygen and sulfur hetero-atoms. Where there are 3 hetero-atoms, we prefer that at least one (more preferably 2) should be a nitrogen atom and one or two should be nitrogen, oxygen or sulfur atoms (and, where there are two, they may be the same or different). Where there are two hetero-atoms, these may be the same or different and they are selected from nitrogen, oxygen and sulfur atoms; however, more preferably one is a nitrogen atom or an oxygen atom and the other is a nitrogen, oxygen or sulfur atom. Such groups may be unsubstituted or they may be substituted by at least one (preferably from 1 to 3) of substituents (c), defined above. Examples of such unsubstituted groups include the aziridinyl, azetidinyl, pyrrolidinyl, piperidyl, morpholinyl, oxiranyl, oxetanyl, tetrahydrofuryl, tetrahydropyranyl, dioxolanyl (especially 1,3-dioxolanyl), oxazolidinyl, oxazolinyl (4,5-dihydrooxazolyl), oxazolyl, isoxazolyl, thiazolidinyl, thiazolyl, thiiranyl, thietanyl and tetrahydrothienyl groups. As noted above, such groups may be unsubstituted or they may be substituted by at least one of substituents (b). For example, where the substituent is an oxygen atom, examples of such substituted groups include the S-oxothiiranyl, S-oxothietanyl, S-oxotetrahydrothienyl, S,S-dioxothietanyl, S,S-dioxotetrahydrothienyl, oxoazetidinyl and oxopyrrolidinyl groups.

Where $R^2$ represents an alkyl group having a cycloalkyl or heterocyclic substituent, the alkyl group most preferably has from 1 to 3 carbon atoms, i.e. is preferably a methyl, ethyl or propyl group, in the case of the cycloalkyl-substituted group, or a methyl, ethyl, propyl or isopropyl group, in the case of the heterocyclic-substituted group.

Preferred examples of groups which may be represented by $R^2$ include the 2-hydroxyethyl, 3hydroxypropyl, 2,3-dihydroxypropyl, 2-aminoethyl, 3-amino-2-hydroxypropyl, 2-amino-1-methylethyl, carboxymethyl, methoxycarbonylmethyl, 2-carboxyethyl, carbamoylmethyl, 2-carbamoylethyl, 2-carbamoyl-2-hydroxyethyl, cyanomethyl, 2-hydroxyiminoethyl, 2-amino-2-carboxyethyl, 1-carboxyethyl, 2-hydroxy-1-methylethyl, 2-amino-2-carboxy-1-methylethyl, 1-cyanoethyl, 1-methyl-2-methoxyiminoethyl, 2-carbamoyl-1-methylethyl, 2-hydroxycyclopropyl, 3-aminocyclobutyl, -carboxycyclopentyl, (2-aminocyclopropyl)methyl, (3-carbamoylcyclobutyl)m- ethyl, 1-(3-formamidocyclobutyl)ethyl, 3-azetidinyl, 1-formyl-3-pyrrolidinyl, 5-carbamoyl-3-pyrrolidinyl, 4-oxo-2-azetidinyl, 2-oxo-3-pyrrolidinyl, 5-(hydroxymethyl)-2-oxo-3-pyrrolidinyl, 1-(2-oxo-3-azetidinyl)ethyl, (1-formyl-2-pyrrolidinyl)methyl, (5-oxo-2-pyrrolidinyl)methyl, 5-carboxy-3-pyrrolidinyl, 3-carbamoylcyclobutyl, 2-aziridinylmethyl, 2-oxiranylmethyl, 2-oxetanylmethyl, 1-(2-oxetanyl)ethyl, 3-oxetanyl, (3-hydroxy-2-oxetanyl)methyl, 4,5-dihydrooxazol-5-ylmethyl, 1,3-dioxolan-2-yl-methyl, 4,5-dihydrooxazol-2-ylmethyl, 5-oxazolylmethyl, 1-(2-oxazolyl)ethyl, (2-amino-5-oxazolyl)methyl, 5-isoxazolylmethyl, 1-(3-isoxazolyl)ethyl and (2-amino-4-thiazolyl)methyl groups.

A preferred class of compounds of the present invention are those compounds of formula (I) in which:

Ar represents a chlorophenyl, dichlorophenyl, difluorophenyl, chlorofluorophenyl, (trifluoromethyl)phenyl, chloro(trifluoromethyl)phenyl or fluoro(trifluoromethyl)phenyl group;

$R^1$ represents a methyl, ethyl or propyl group;

$R^2$ represents:

a methyl, ethyl, propyl or isopropyl group which is substituted by at least one substituent selected from the group consisting of substituents (a), as defined above;

a cyclopropyl, cyclobutyl or cyclopentyl group which is substituted by at least one substituent selected from the group consisting of substituents (b), as defined above;

a cyclopropylmethyl, cyclopropylethyl, cyclobutylmethyl, cyclobutylethyl, cyclopentylmethyl or cyclopentylethyl group whose cycloalkyl part is substituted by at least one substituent selected from the group consisting of substituents (b), as defined above;

an aziridinyl, azetidinyl, pyrrolidinyl, oxiranyl, oxetanyl, tetrahydrofuryl, 1,3-dioxolanyl, oxazolinyl, oxazolyl, isoxazolyl, thiazolidinyl, thiazolyl, thietanyl, tetrahydrothienyl, S-oxothietanyl or S,S-dioxothietanyl group which is unsubstituted or is substituted by at least one substituent selected from the group consisting of substituents (b), as defined above; or an aziridinylmethyl, aziridinylethyl, azetidinylmethyl, azetidinylethyl, pyrrolidinylmethyl, pyrrolidinylethyl, oxiranylmethyl, oxiranylethyl, oxetanylmethyl, oxetanylethyl, tetrahydrofurylmethyl, tetrahydrofurylethyl, 1,3-dioxolanylmethyl, 1,3-dioxolanylethyl, oxazolinylmethyl, oxazolinylethyl, oxazolylmethyl, oxazolylethyl, isoxazolylmethyl, isoxazolylethyl, thiazolidinylmethyl, thiazolidinylethyl, thiazolylmethyl, thiazolylethyl, thietanylmethyl, thietanylethyl, tetrahydrothienylmethyl, tetrahydrothienylethyl, S-oxothietanylmethyl, S-oxothietanylethyl, S,S-dioxothietanylmethyl or S,S-dioxothietanylethyl group whose heterocyclic part is unsubstituted or is substituted by at least one substituent selected from the group consisting of substituents (b), as defined above.

A more preferred class of compounds of the present invention are those compounds of formula (I) in which:

Ar represents a 4-chlorophenyl, 2,4-dichlorophenyl, 2,4-difluorophenyl or 4-chloro-2-fluorophenyl group;

$R^1$ represents a methyl or ethyl group;

$R^2$ represents:

a methyl, ethyl, propyl or isopropyl group which is substituted by at least one substituent selected from the group consisting of substituents (a), as defined above;

a cyclopropyl, cyclobutyl or cyclopentyl group which is substituted by at least one substituent selected from the group consisting of substituents (b), as defined above;

a cyclopropylmethyl, cyclopropylethyl, cyclobutylmethyl or cyclopentylmethyl group whose cycloalkyl part is substituted by at least one substituent selected from the group consisting of substituents (b), as defined above;

an aziridinyl, azetidinyl, oxiranyl, oxetanyl, tetrahydrofuryl, 1,3-dioxolanyl, oxazolinyl, oxazolyl, thiazolyl, thietanyl, tetrahydrothienyl, S-oxothietanyl or S,S-dioxothietanyl group which is unsubstituted or is substituted by at least one substituent selected from the group consisting of substituents (b), as defined above; or an aziridinylmethyl, azetidinylethyl, pyrrolidinylmethyl, oxiranylmethyl, oxiranylethyl, oxetanylmethyl, oxetanylethyl, tetrahydrofurylmethyl, 1,3-dioxolanylethyl, oxazolinylmethyl, oxazolylmethyl, isoxazolylmethyl, thiazolidinylmethyl, thiazolylmethyl, thietanylmethyl, tetrahydrothienylmethyl, S-oxothietanylmethyl or S,S-dioxothietanylmethyl group whose heterocyclic part is unsubstituted or is substituted by at least one substituent selected from the group consisting of substituents (b), as defined above.

A still more preferred class of compounds of the present invention are those compounds of formula (I) in which:

Ar represents a 4-chlorophenyl, 2,4-dichlorophenyl, 2,4-difluorophenyl or 4-chloro-2-fluorophenyl group;

$R^1$ represents a methyl group;

$R^2$ represents:

a methyl, ethyl, propyl or isopropyl group which is substituted by at least one substituent selected from the group consisting of substituents (d), defined below;

a cyclopropyl, cyclobutyl or cyclopentyl group which is substituted by at least one substituent selected from the group consisting of substituents (d), defined below;

a cyclopropylmethyl, cyclopropylethyl, cyclobutylmethyl or cyclopentylmethyl group whose cycloalkyl part is substituted by at least one substituent selected from the group consisting of substituents (d), defined below;

an aziridinyl, azetidinyl, oxiranyl, oxetanyl, tetrahydrofuryl, 1,3-dioxolanyl, oxazolinyl, oxazolyl, thiazolyl, thietanyl, tetrahydrothienyl, S-oxothietanyl or S,S-dioxothietanyl group which is unsubstituted or is substituted by at least one substituent selected from the group consisting of substituents (e), defined below; or an aziridinylmethyl, azetidinylethyl, pyrrolidinylmethyl, oxiranylmethyl, oxiranylethyl, oxetanylmethyl, oxetanylethyl, tetrahydrofurylmethyl, 1,3-dioxolanylethyl, oxazolinylmethyl, oxazolylmethyl, isoxazolylmethyl, thiazolidinylmethyl, thiazolylmethyl, thietanylmethyl, tetrahydrothienylmethyl, S-oxothietanylmethyl or S,S-dioxothietanylmethyl group whose heterocyclic part is unsubstituted or is substituted by at least one substituent selected from the group consisting of substituents (e), defined below.

substituents (d):

groups of formula —$OR^3$, where $R^3$ represents a hydrogen atom or an alkyl group having from 1 to 4 carbon atoms;

groups of formula =$NOR^4$, where $R^4$ represents a hydrogen atom or an alkyl group having from 1 to 4 carbon atoms;

groups of formula —$NHCOR^8$, where $R^8$ represents a hydrogen atom;

groups of formula —COOR$^9$, where R$^9$ represents a hydrogen atom or an alkyl group having from 1 to 4 carbon atoms;

groups of formula —CONR$^{10}$R$^{11}$, where R$^{10}$ and R$^{11}$ are the same or different and each represents a hydrogen atom or an alkyl group having from 1 to 4 carbon atoms;

groups of formula —S(O)$_m$R$^{12}$, where R$^{12}$ represents an alkyl group having from 1 to 4 carbon atoms and m is 0, 1 or 2; and cyano groups;

substituents (e):

groups of formula —OR$^3$, where R$^3$ is as defined above;

groups of formula —S(O)$_m$R$^{12}$, where R$^{12}$ and m are as defined above;

oxygen atoms; and formyl and hydroxymethyl groups.

The most preferred class of compounds of the present invention are those compounds of formula (I) in which:

Ar represents a 4-chlorophenyl, 2,4-dichlorophenyl, 2,4-difluorophenyl or 4-chloro-2-fluorophenyl group;

R$^1$ represents a methyl group;

R$^2$ represents:

a methyl, ethyl or propyl group which is substituted by at least one substituent selected from the group consisting of substituents (f), defined below;

a cyclopropyl or cyclobutyl group which is substituted by at least one substituent selected from the group consisting of substituents (f), defined below;

a cyclopropylmethyl or cyclopropylethyl group whose cycloalkyl part is substituted by at least one substituent selected from the group consisting of substituents (f), defined below;

an oxiranyl, oxetanyl, tetrahydrofuryl, 1,3-dioxolanyl, oxazolinyl, thietanyl, tetrahydrothienyl, S-oxothietanyl or S,S-dioxothietanyl group which is unsubstituted or is substituted by at least one substituent selected from the group consisting of substituents (e), defined above; or an azetidinylethyl, oxiranylmethyl, oxetanylmethyl, oxazolinylmethyl, thietanylmethyl or S,S-dioxothietanylmethyl group whose heterocyclic part is unsubstituted or is substituted by at least one substituent selected from the group consisting of substituents (e), defined above;

substituents (f):

groups of formula —OR$^3$, where R$^3$ represents a hydrogen atom or an alkyl group having from 1 to 4 carbon atoms;

groups of formula —S(O)$_m$R$^{12}$, where R$^{12}$ represents an alkyl group having from 1 to 4 carbon atoms and m is 0, 1 or 2; and cyano groups.

Specific examples of individual preferred compounds of the present invention are those compounds of formula (I) in which the substituents are as defined in the following Table 1. In the Table, the following abbreviations are used for certain of the substituent groups:

| Azr | aziridinyl |
| Azt | azetidinyl |
| Bu | butyl |
| cBu | cyclobutyl |
| Car | carbamoyl |
| Dhox | 4,5-dihydrooxazolyl |
| Dix | 1,3-dioxolanyl |
| Et | ethyl |
| Fo | formyl |
| Isox | isoxazolyl |
| Me | methyl |
| Oxa | oxazolyl |
| Oxr | oxiranyl |
| Oxt | oxetanyl |
| Ph | phenyl |
| cPn | cyclopentyl |
| Pr | propyl |
| cPr | cyclopropyl |
| Pyrd | pyrrolidinyl |
| Thiz | thiazolyl |

TABLE 1

| Cpd. No. | Ar | R$^1$ | R$^2$ | n |
|---|---|---|---|---|
| 1 | p-ClPh | Me | HOOC.CH$_2$— | 0 |
| 2 | p-ClPh | Me | 2-HOOC.Et | 1 |
| 3 | p-ClPh | Me | Car.CH$_2$— | 1 |
| 4 | p-ClPh | Me | 2-Car-2-HO.Et | 0 |
| 5 | p-ClPh | Me | 2-HO.Et | 1 |
| 6 | p-ClPh | Me | 2-H$_2$N.Et | 2 |
| 7 | p-ClPh | Me | 2,4-diHO.Bu | 0 |
| 8 | p-ClPh | Me | 3-HO-1-Me.Et | 2 |
| 9 | p-ClPh | Me | 1-(HON=CH)Et | 0 |
| 10 | p-ClPh | Me | NC.CH$_2$— | 2 |
| 11 | p-ClPh | Me | 2-HO.cPr | 1 |
| 12 | p-ClPh | Me | 3-HOOC.cPn | 0 |
| 13 | p-ClPh | Me | (2-H$_2$N.cPr).CH$_2$— | 2 |
| 14 | p-ClPh | Me | 2-Azt | 1 |
| 15 | p-ClPh | Me | 1-Fo-3-Pyrd | 0 |
| 16 | p-ClPh | Me | 5-Car-3-Pyrd | 2 |
| 17 | p-ClPh | Me | 2-oxo-3-Pyrd | 0 |
| 18 | p-ClPh | Me | (1-Fo-2-Pyrd).CH$_2$— | 2 |
| 19 | p-ClPh | Et | Car.CH$_2$— | 0 |
| 20 | p-ClPh | Et | HON=CHCH$_2$— | 2 |
| 21 | p-ClPh | Et | 3-HOPr | 1 |
| 22 | p-ClPh | Et | MeO.CH$_2$— | 0 |
| 23 | p-ClPh | Et | 2-HOOC-2-NH$_2$—Et | 0 |
| 24 | p-ClPh | Et | 3-Car.cBu | 2 |
| 25 | 2,4-diClPh | Me | HOOC.CH$_2$— | 0 |
| 26 | 2,4-diClPh | Me | 3-HOPr | 2 |
| 27 | 2,4-diClPh | Me | 3-NH$_2$-2-HOPr | 1 |
| 28 | 2,4-diClPh | Me | 2-NH$_2$-1-MeEt | 0 |
| 29 | 2,4-diClPh | Me | 1-NC.Et | 2 |
| 30 | 2,4-diClPh | Me | 2-NH$_2$-2-HOOC-1-MeEt | 0 |
| 31 | 2,4-diClPh | Me | 5-HOOC-3-Pyrd | 2 |
| 32 | 2,4-diClPh | Me | MeON=CHCH$_2$— | 0 |
| 33 | 2,4-diClPh | Me | 3-NH$_2$.cBu | 2 |
| 34 | 2,4-diClPh | Me | 1-(3-FoNH.cBu)Et | 1 |
| 35 | 2,4-diFPh | Me | 2-HO.Et | 0 |
| 36 | 2,4-diFPh | Me | 2-HO.Et | 2 |
| 37 | 2,4-diFPh | Me | Car.CH$_2$— | 0 |
| 38 | 2,4-diFPh | Me | 1-Car.Et | 2 |
| 39 | 2,4-diFPh | Me | 2-NH$_2$.Et | 0 |
| 40 | 2,4-diFPh | Me | HON=CHCH$_2$— | 0 |
| 41 | 2,4-diFPh | Me | NC.CH$_2$— | 2 |
| 42 | 2,4-diFPh | Me | 3-NH$_2$-2-HOPr | 0 |
| 43 | 2,4-diFPh | Me | HOOC.CH$_2$— | 1 |
| 44 | 2,4-diFPh | Me | MeOOC.CH$_2$— | 2 |
| 45 | 2,4-diFPh | Me | 2-HO.cPr | 0 |
| 46 | 2,4-diFPh | Me | 2-NH$_2$-1-MeEt | 0 |
| 47 | 2,4-diFPh | Me | 2-NH$_2$-2-HOOC—Et | 2 |
| 48 | 2,4-diFPh | Me | 1-(MeON=CH—)Et | 0 |
| 49 | 2,4-diFPh | Me | Car.CH$_2$— | 2 |
| 50 | 2,4-diFPh | Me | 5-HOOC-3-Pyrd | 0 |
| 51 | 2,4-diFPh | Me | 3-Azt | 0 |
| 52 | 2,4-diFPh | Me | 2-HO.cPr | 2 |
| 53 | 2,4-diFPh | Me | 3-NH$_2$.cBu | 0 |
| 54 | 2,4-diFPh | Me | (2-NH$_2$.cPr).CH$_2$— | 0 |
| 54 | 2,4-diFPh | Me | 1-Fo-3-Pyrd | 2 |
| 55 | 2,4-diFPh | Me | 5-Car-3-Pyrd | 0 |
| 56 | 2,4-diFPh | Me | (3-Car.cBu)CH$_2$— | 2 |

TABLE 1-continued

| Cpd. No. | Ar | R¹ | R² | n |
|---|---|---|---|---|
| 58 | 2,4-diFPh | Me | (1-Fo-2-Pyrd)CH₂— | 0 |
| 59 | 2,4-diFPh | Me | 4-oxo-2-Azt | 0 |
| 60 | 2,4-diFPh | Me | 2-oxo-3-Pyrd | 2 |
| 61 | 2,4-diFPh | Me | 5-HOMe-3-Pyrd | 0 |
| 62 | 2,4-diFPh | Me | (5-oxo-2-Pyrd)CH₂— | 2 |
| 63 | 2,4-diFPh | Me | 1-(2-oxo-3-Azt)Et | 0 |
| 64 | 2,4-diFPh | Me | 3-Car.cBu | 0 |
| 65 | 2,4-diFPh | Me | 2-Car-2-HO.Et | 2 |
| 66 | 2,4-diFPh | Me | (2-Azr)CH₂— | 0 |
| 67 | 2,4-diFPh | Me | (2-Oxr)CH₂— | 2 |
| 68 | 2,4-diFPh | Me | (2-Oxt)CH₂— | 0 |
| 69 | 2,4-diFPh | Me | 1-(3-Oxt)Et | 1 |
| 70 | 2,4-diFPh | Me | (3-HO-2-Oxt)CH₂— | 2 |
| 71 | 2,4-diFPh | Me | (2-Dix)CH₂— | 0 |
| 72 | 2,4-diFPh | Me | (2-Dhox)CH₂— | 0 |
| 73 | 2,4-diFPh | Me | (5-Oxa)CH₂— | 0 |
| 74 | 2,4-diFPh | Me | 1-(2-Oxa)Et | 2 |
| 75 | 2,4-diFPh | Me | (2-NH₂-5-Oxa)CH₂— | 1 |
| 76 | 2,4-diFPh | Me | 1-(3-Isox)Et | 2 |
| 77 | 4-Cl-2-FPh | Me | 2-HOEt | 0 |
| 78 | 4-Cl-2-FPh | Me | CarCH₂— | 2 |
| 79 | 4-Cl-2-FPh | Me | HON=CH.CH₂— | 0 |
| 80 | 4-Cl-2-FPh | Me | 2-NH₂Et | 0 |
| 81 | 4-Cl-2-FPh | Me | 2-NH₂-2-HOOC.Et | 2 |
| 82 | 2-Cl-4-FPh | Me | NC.CH₂— | 0 |
| 83 | 2-Cl-4-FPh | Me | 4-oxa-2-Azt | 0 |
| 84 | 2-Cl-4-FPh | Me | 3-Azt | 2 |
| 85 | 2-Cl-4-FPh | Me | 1-Fo-3-Pyrd | 0 |
| 86 | 2-Cl-4-FPh | Me | 5-Car-3-Pyrd | 2 |
| 87 | 2-Cl-4-FPh | Me | 2-oxo-3-Pyrd | 0 |
| 88 | 2-Cl-4-FPh | Me | MeON=CH.CH₂— | 0 |
| 89 | 2-Cl-4-FPh | Me | 2-Oxr.CH₂— | 0 |
| 90 | 2-Cl-4-FPh | Me | 1-(3-Oxt)Et | 0 |
| 91 | 2-Cl-4-FPh | Me | (2-Dhox)CH₂— | 2 |
| 92 | 2-Cl-4-FPh | Me | 1-(2-Oxa)Et | 2 |
| 93 | 2-Cl-4-FPh | Me | (2-NH₂-5-Oxa)CH₂— | 0 |
| 94 | 2-Cl-4-FPh | Me | (5-Isox)CH₂— | 2 |
| 95 | 2-Cl-4-FPh | Me | 1-(3-Isox)Et | 0 |
| 96 | 2-Cl-4-FPh | Me | (4-Thiz)CH₂— | 2 |
| 97 | 2-Cl-4-FPh | Me | (2-NH₂-4-Thiz)CH₂— | 2 |
| 98 | 2-Cl-4-FPh | Et | 2-Azr.CH₂— | 0 |
| 99 | 2-Cl-4-FPh | Et | 2-Oxa.CH₂— | 1 |
| 100 | 2-Cl-4-FPh | Et | (2-NH₂-4-Thiz)CH₂— | 2 |
| 101 | p-ClPh | Me | 1-NC.Et | 0 |
| 102 | p-ClPh | Me | 1-MeOEt | 0 |
| 103 | p-ClPh | Me | MeSCH₂— | 0 |
| 104 | p-ClPh | Me | 3-thietanyl | 1 |
| 105 | 2,4-diClPh | Me | 3-Oxt | 0 |
| 106 | 2,4-diFPh | Me | 1-NC.Et | 1 |
| 107 | 2,4-diFPh | Me | MeOCH₂— | 0 |
| 108 | 2,4-diFPh | Me | 1-MeO.Et | 0 |
| 109 | 2,4-diFPh | Me | MeSCH₂— | 0 |
| 110 | 2,4-diFPh | Me | 3-thietanyl | 0 |
| 111 | 2,4-diFPh | Me | S-oxothietan-3-yl | 0 |
| 112 | 2,4-diFPh | Me | S,S-dioxothietan-3-yl | 0 |
| 113 | 2,4-diFPh | Me | 3-tetrahydrofuryl | 2 |
| 114 | 2,4-diFPh | Me | NC.CH₂— | 1 |
| 115 | 2,4-diFPh | Me | 3-tetrahydrofuryl | 0 |
| 116 | 2,4-diFPh | Me | 3-Oxt | 0 |

Of the compounds listed above, the following are preferred, that is to say Compounds No. 5, 10, 11, 22, 29, 35, 41, 45, 55, 59, 63, 67, 68, 69, 77, 82, 83, 85, 89, 90, 99, 101, 102, 104, 105, 103, 106, 107, 108, 109, 110, 111, 112, 113, 114, 115 and 116, of which Compounds No. 10, 22, 29, 41, 67, 68, 69, 82, 83, 89, 90, 99, 101, 102, 104, 105, 103, 106, 107, 108, 109, 110, 111, 112, 114, 115 and 116 are preferred. The most preferred compounds are Compounds No.:

41. 3-(Cyanomethylsulfonyl)-2-(2,4-difluorophenyl)-1-(1H-1,2,4-triazol-1-yl)-2-butanol;
101. 3-[(1-Cyanoethyl)thio]-2-(4-chlorophenyl)-1-(1H-1,2,4-triazol-1-yl)-2 -butanol;
102. 2-(4-Chlorophenyl)-3-[(1-methoxyethyl)thio]-1-(1H-1,2,4-triazol-1-yl)-2 -butanol;
104. 2-(4-Chlorophenyl)-3-[(3-thietanyl)sulfinyl]-1-(1H-1,2,4-triazol-1-yl)-2 -butanol;
105. 2-(2,4-Dichlorophenyl)-3-[(3-oxetanyl)thio]-1-(1H-1,2,4-triazol-1-yl)-2 -butanol,
108. 2-(2,4-Difluorophenyl)-3-[(1-methoxyethyl)thio]-1-(1H-1,2,4-triazol-1-yl)-2 -butanol,
110. 2-(2,4-Difluorophenyl)-3-[(3-thietanyl)thio]-1-(1H-1,2,4-triazol-1-yl)-2 -butanol;
111. 2-(2,4-Difluorophenyl)-3-[(S-oxothietan-3-yl)thio]-1-(1H-1,2,4-triazol-1 -yl)-2-butanol;
112. 2-(2,4-Difluorophenyl)-3-[(S,S-dioxothietan-3-yl)thio]-1-(1H-1,2,4-triazol-1 -yl)-2-butanol;
114. 3-(Cyanomethylsulfinyl)-2-(2,4-difluorophenyl)-1-(1H-1,2,4-triazol-1-yl)-2-butanol;
115. 2-(2,4-Difluorophenyl)-3-(tetrahydrofuran-3-ylthio)-1-(1H-1,2,4-triazol-1-yl)-2 -butanol;
116. 2-(2,4-Difluorophenyl)-3-(oxetan-3-ylthio)-1-(1H-1,2,4-triazol-1-yl)-2-butanol;

and pharmaceutically acceptable salts thereof.

The compounds of the present invention may be prepared by a variety of methods which, in themselves, are well known for the preparation of compounds of this type. For example, in general terms, a suitable method comprises reacting a compound of formula (II):

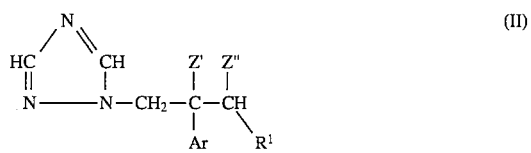

(II)

[in which Ar and R¹ are as defined above, and either Z' represents a hydroxy group and Z" represents a mercapto group or Z' and Z" together represent an oxygen atom (to form an epoxy group)] with a compound of formula (III):

$$X—R^2 \qquad (III)$$

(in which R² is as defined above, and, when Z' represents a hydroxy group and Z" represents a mercapto group, X represents a halogen atom, a sulfonyloxy group or a carboxylic acyloxy group, or when Z' and Z" together represent an oxygen atom, X represents a mercapto group);

or with a compound of formula (III) in which an active group other than said group X is protected, to give a compound of formula (I) in which n is 0;

and, optionally, oxidizing said compound of formula (I) in which n is 0, to give a compound of formula (I) in which n is 1 or 2;

and, optionally, removing any protecting group.

In more detail, the reaction to prepare the compounds of the present invention may be carried out as described in either of the following Methods A and B.

Method A:

In this reaction, a compound of formula (II'):

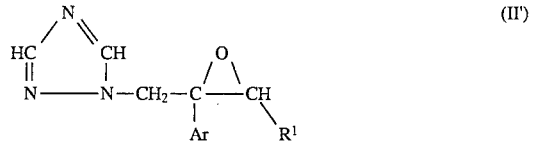

(II')

(in which Ar and R¹ are as defined above) is reacted with a compound of formula (III'):

$$HS—R^2 \qquad (III')$$

(in which R² is as defined above) or with a compound of formula (III) in which an active group other than said group X is protected, to give a compound of formula (I) in which n is 0.

In particular, where $R^2$ represents an alkylamino group, we prefer that this group should be protected. Protecting groups which may be used in this reaction are well known in the art and any which is capable of use with known reactions of this type may equally be used here. For example, suitable protecting groups include: lower aliphatic carboxylic acyl groups, such as the formyl, acetyl or propionyl groups; carbocyclic aromatic, carboxylic acyl groups, such as the benzoyl group; and lower alkoxycarbonyl groups, such as the t-butoxycarbonyl group. The protecting group may be introduced by well known means, for example as described in "Protective Groups in Organic Synthesis" by T. W. Greene (John Wiley & Sons Inc., 1981), the disclosure of which is incorporated herein by reference.

The epoxide compound of formula (II'), which is one of the starting materials for use in the present invention, is described in U.S. patent application No. 319145 and its equivalent EP-A-332387, the disclosures of which are incorporated herein by reference, and may be prepared as described in those references.

The reaction of the epoxide compound of formula (II') with the mercapto compound of formula (III') normally and preferably is effected in a solvent, under basic conditions. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol and propanol; amides, especially fatty acid amides, such as dimethylformamide and dimethylacetamide; sulfoxides, such as dimethyl sulfoxide; nitriles, such as acetonitrile; and ethers, such as tetrahydrofuran and dioxane; and mixtures of water with any one or more of these organic solvents. Examples of bases which may be employed in the reaction include: alkali metal hydrides, such as sodium hydride; alkali metal alkoxides, such as sodium methoxide, sodium ethoxide, lithium methoxide and potassium t-butoxide; and alkali metal hydroxides, such as lithium hydroxide, sodium hydroxide and potassium hydroxide. There is no particular restriction on the amount of alkali employed, but, in general, we prefer to employ from 0.1 to 2 moles of alkali per mole of the compound of formula (II'). The amount of the mercapto compound of formula (III') employed in the reaction is preferably from 1 to 3 molar equivalents.

The reaction can take place over a wide range of temperatures, and the precise reaction temperature is not critical to the invention. In general, we find it convenient to carry out the reaction at a temperature of from about room temperature to 100° C. The time required for the reaction may also vary widely, depending on many factors, notably the reaction temperature and the nature of the reagents. However, provided that the reaction is effected under the preferred conditions outlined above, a period of from 2 to 10 hours will usually suffice.

Where $R^2$ contains a protected group, e.g. a protected amino or alkylamino group, the desired compound of formula (I) in which n is 0 can be prepared by deprotecting the product. Where the protecting group is an acyl group, this may be removed by treating the protected compound with an acid or base by conventional means. Where the protecting group is a t-butoxycarbonyl group, this may be removed by treating the protected compound with an acid by conventional means, for example as described in "Protective Groups in Organic Synthesis".

Method B:

The compound of formula (I) of the present invention in which n is 0 can be also prepared by reacting a compound of formula (II"):

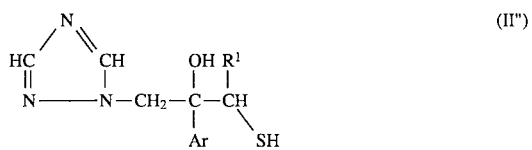

(in which Ar and $R^1$ are as defined above) with a compound of formula (III"):

$$R^2—X' \qquad (III'')$$

(in which $R^2$ is defined above and X' represents a halogen atom, a sulfonyloxy group or a carboxylic acyloxy group) or, especially where $R^2$ includes an amino or alkylamino group, with a compound of formula (III") in which any such active group, other than the group X', is protected. Examples of such protected groups are as given in Method A. X' represents: a halogen atom, such as a chlorine, bromine or iodine atom; a sulfonyloxy group, such as a lower alkanesulfonyloxy group or haloalkanesulfonyloxy group (e.g. a methanesulfonyloxy or trifluoromethanesulfonyloxy group) or an aranesulfonyloxy group (e.g. a benzenesulfonyloxy or toluenesulfonyloxy, especially p-toluenesulfonyloxy group); or an acyloxy group, such as an acetoxy group).

In this Method, the desired compound of formula (I) can be prepared by reacting a triazolylmercaptoalcohol derivative of formula (II") with an alkylating agent of formula (III") under basic conditions. The triazolylmercaptoalcohol derivative of formula (II") is described in Japanese Patent Application (Tokugan) No. Hei 2-35928, the disclosure of which is incorporated herein by reference, and may be prepared as disclosed in that reference. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol, propanol and butanol; amides, especially fatty acid amides, such as dimethylformamide and dimethylacetamide; sulfoxides, such as dimethyl sulfoxide; nitriles, such as acetonitrile; ethers, such as tetrahydrofuran, dioxane and diethyl ether; ketones, such as acetone; and hydrocarbons, especially aromatic hydrocarbons, such as benzene, toluene and xylene. Examples of bases which may be employed in the reaction include: organic amines, such as triethylamine and diisopropylethylamine; alkali metal hydrides, such as sodium hydride; alkali metal alkoxides, such as sodium methoxide, sodium ethoxide, lithium methoxide and potassium t-butoxide; and alkali metal hydroxides, such as sodium hydroxide and potassium hydroxide. Although the amount of the base employed in the reaction is not critical, we prefer to employ from 1 to 3 moles per mole of the compound of formula (II"). The amount of the alkylating agent of formula (III") employed in the reaction is also not critical, but we prefer to employ from 1 to 3 molar equivalents.

The reaction can take place over a wide range of temperatures, and the precise reaction temperature is not critical to the invention. In general, we find it convenient to carry out the reaction at a temperature of from –50° C. to 100° C. The time required for the reaction may also vary widely, depending on many factors, notably the reaction temperature and the nature of the reagents. However, provided that the reaction is effected under the preferred conditions outlined above, a period of from 2 to 10 hours will usually suffice.

Where $R^2$ includes a protected group, e.g. a protected amino or alkylamino group, the protecting group can be removed as described in Method A.

Compounds of formula (I) in which n is 1 or 2 can be prepared by oxidizing the corresponding compound of formula (I) in which n is 0. The predominant product will depend upon the amount of oxidizing agent employed. That is, compounds of formula (I) in which B is 1, can be prepared by oxidizing the compound of formula (I) in which n is 0 with about one equivalent of an oxidizing agent in the presence of a solvent, and compounds of formula (I) in which 5 is 2 can be prepared by oxidation using two or more equivalents of an oxidizing agent. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, especially halogenated aliphatic hydrocarbons, such as methylene chloride or chloroform. Examples of suitable oxidizing agents include: peracetic acid and 3-chloroperbenzoic acid. The reaction can take place over a wide range of temperatures, and the precise reaction temperature is not critical to the invention. In general, we find it convenient to carry out the reaction at a temperature of from 0° C. to 50° C., preferably at about room temperature. The time required for the reaction may also vary widely, depending on many factors, notably the reaction temperature and the nature of the reagents. However, provided that the reaction is effected under the preferred conditions outlined above, a period of from 30 minutes to 3 hours will usually suffice.

At the end of any of the above reactions, the reaction product can be recovered from the reaction mixture by conventional means. If desired, it can then be further purified by conventional means, for example by recrystallisation or by one of the chromatography techniques, such as column chromatography or preparative thin layer chromatography.

The compounds of the present invention have demonstrated valuable anti-fungal activity, as shown hereafter, and can be used for the treatment and prophylaxis of fungal infections in humans and other animals. They have also shown antibiotic activity against trichophyton species. They may be administered orally, parenterally or topically, and, if desired, may be formulated with conventional pharmaceutically acceptable adjuvants, such as carriers, excipients, dispersants and diluents, for the preparation of appropriate pharmaceutical formulations. The dose and frequency of administration will depend upon the condition, age, and body weight of the patient as well as upon the nature and severity of the disorder to be treated, but in the case of oral administration to an adult human patient, we would normally suggest a total daily dose of from 50 mg to 2000 mg, more preferably from 100 to 600 mg, which may be administered in a single dose or in divided doses, e.g. from one to three times a day.

The invention is further illustrated by the following Examples, which show the preparation of certain of the compounds of the present invention, and the subsequent Experiment, which demonstrates the biological activity of the compounds. In these Examples, the formulae of the title compounds are given by way of guidance, but it should be noted that these formulae disregard any steric configurations.

EXAMPLE 1

(2R,3R)-2-(2,4-Difluorphenyl)-3-[(2-hydroxyethyl)-thio]-1-(1H-1,2,4-triazol- 1-yl)-2-butanol

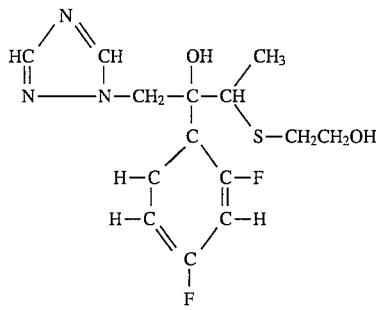

70 mg (1.60 mmole) of sodium hydride (as a 55% w/w dispersion in mineral oil) were washed with hexane, and then suspended in 3 ml of dimethylformamide. 187 mg (2.4 mmole) of 2-mercaptoethanol were added to the resulting suspension under an atmosphere of nitrogen, whilst ice-cooling, and the mixture was stirred for 10 minutes. At the end of this time, 200 mg (0.80 mmole) of (2R,3S)-2-(2,4-difluorophenyl)-3-methyl-2-[(1H-1,2,4-triazol-1-yl)methyl] oxirane (prepared as described in European Patent Publication 332 387, the disclosure of which is incorporated herein by reference) were added to the mixture, and the resulting mixture was stirred at 50°–60° C. for 30 minutes. The mixture was then cooled after which it was diluted with ethyl acetate. It was then washed with a saturated aqueous solution of sodium chloride; and the solvent was then removed by distillation under reduced pressure. The crude product thus obtained was purified by column chromatography through 10 g of silica gel, using a 4:1 by volume mixture of ethyl acetate and hexane as the eluent, to afford 195 mg of the title compound. A pure specimen melting at 89°–90° C. was then obtained by recrystallization from a mixture of ethyl acetate and hexane.

Specific rotation $[\alpha]_D^{25} = -85.9°$ (c=0.58, CHCl$_3$). Infrared Absorption Spectrum (KBr), $\nu_{max}$ cm$^{-1}$: 3447, 3234, 1615. Nuclear Magnetic Resonance Spectrum (CDCl$_3$), δ ppm: 1.14 (3H, doublet, J=7 Hz); 2.6–3.1 (3H, multiplet); 3.45 (1H, quartet, J=7 Hz); 3.83 (2H, triplet, J=6.5 Hz); 4.83 (1H, doublet, J=14.5 Hz); 4.85 (1H, broad); 5.14 (1H, doublet, J=14.5 Hz); 5.51 (1H, singlet); 6.5–7.0 (2H, multiplet); 7.2–7.6 (1H, multiplet); 7.74 (1H, singlet); 8.03 (1H, singlet).

EXAMPLE 2

(2R,3R)-2-(2,4-Difluorophenyl(-3-[(2-hydroxyethyl)-sulfonyl]-1-(1H-1,2,4 -triazol-1-yl)-2-butanol

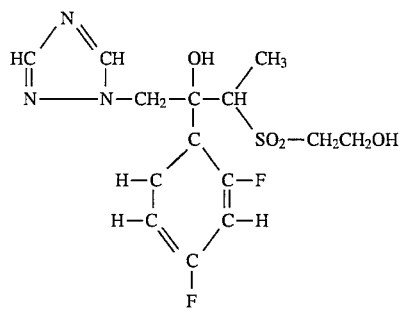

96 mg (0.56 mmole) of 3-chloroperbenzoic acid were added to a solution of 84 mg (0.26 mmole) of (2R,3R)-2-(2,4-difluorophenyl)-3-[(2-hydroxyethyl)thio]-1-(1H-1,2,4-triazol-1 -yl)-2-butanol (prepared as described in Example 1) in 1 ml of methylene chloride, and the mixture was stirred at room temperature for 15 minutes. At the end of this time, the reaction mixture was diluted with ethyl acetate and washed, in turn, with an aqueous solution of sodium sulfite, with a dilute aqueous solution of sodium hydrogencarbonate and with a saturated aqueous solution of sodium chloride. It was then dried, and the crude product obtained by distilling off the solvent was purified by column chromatography through 5 g of silica gel, using a 10:10:1 by volume mixture of ethyl acetate, chloroform and ethanol as the eluent, to afford 63 mg of the title compound as a solid. A pure specimen melting at 122° C. was obtained by recrystallization of this solid from a mixture of ethyl acetate and benzene.

Specific rotation $[\alpha]_D^{25}$=−55.8° (c=0.48, CHCl$_3$). Infrared Absorption Spectrum (KBr), $v_{max}$ cm$^{-1}$: 3389, 1616. Nuclear Magnetic Resonance Spectrum (CDCl$_3$), δ ppm: 1.27 (3H, doublet, J=7 Hz); 3.3 (1H, broad); 3.4–3.6 (2H, multiplet); 3.76 (1H, quartet, J=7 Hz); 4.22 (2H, triplet, J=6 Hz); 5.01 (1H, doublet, J=14 Hz); 5.43 (1H, doublet, J=14 Hz); 5.6 (1H, broad); 6.6–7.0 (2H, multiplet); 7.1–7.6 (1H, multiplet); 7.79 (1H, singlet); 7.90 (1H, singlet).

EXAMPLE 3

(2R*,3R*)-2-(2,4-Difluorophenyl)-3-[(3-hydroxypropyl)thio]-1-(1H-1,2,4-triazol-1-yl)-2-butanol

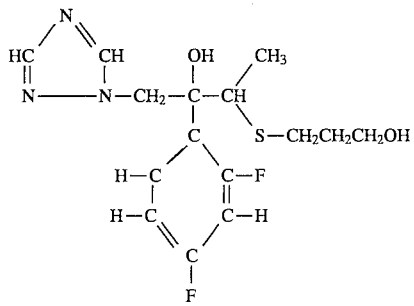

Following a procedure similar to that described in Example 1, but using 50 mg of (2R*,3R*)-2-(2,4-difluorophenyl)-3-methyl-2-[(1H- 1,2,4-triazol-1-yl)methyl]oxirane [prepared as described in Chem. Pharm. Bull., 38, 2476 (1990), Oida et al.] and 54 mg of 3-mercaptopropanol, 42 mg of the title compound, melting at 119°–120° C. (after recrystallization from a mixture of ethyl acetate and benzene), were obtained.

Infrared Absorption Spectrum (CHCl$_3$), $v_{max}$ cm$^{-1}$: 3420, 1618, 1598, 1500. Nuclear Magnetic Resonance Spectrum (CDCl$_3$), δ ppm: 1.15 (3H, doublet, J=7 Hz); 1.7–2.1 (2H, multiplet); 2.6–3.1 (3H, multiplet); 3.34 (1H, quartet, J=7 Hz); 3.78 (2H, triplet, J=6 Hz); 4.82 (1H, doublet, J=14 Hz); 4.9 (1H, broad); 5.10 (1H, doublet, J=14 Hz); 6.6–7.0 (2H, multiplet); 7.1–7.6 (1H, multiplet); 7.75 (1H, singlet); 7.89 (1H, singlet).

EXAMPLE 4

(2R,3R)-2-(2,4-Difluorophenyl)-3-[(methoxycarbonylmethyl)thio]-1-(1H,-1,2,4-triazol-1-yl)-2-butanol

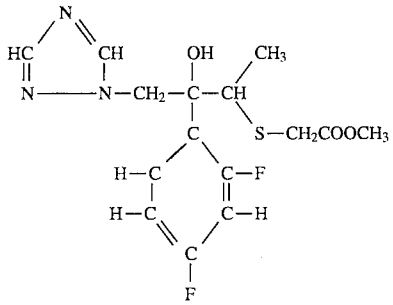

64.2 mg (0.42 mmole) of methyl bromoacetate and 48 mg (0.35 mole) of potassium carbonate were added to a solution of 100 mg (0.35 mmole) of (2R,3R)-2-(2,4-difluorophenyl)-3-mercapto-1-(1H- 1,2,4-triazol-1-yl)-2butanol (prepared as described in Japanese Patent Publication No. Hei 3-128338) in 3 ml of anhydrous dimethylformamide, and the mixture was stirred at room temperature for 1 hour. At the end of this time, the reaction mixture was diluted with benzene and washed with a saturated aqueous solution of sodium chloride; the solvent was then removed by distillation under reduced pressure. The crude product thus obtained was purified by column chromatography through 5 g of silica gel, using a 3:1 by volume mixture of hexane and ethyl acetate as the eluent, to afford 120 mg of the title compound. A pure specimen, melting at 86°–87° C., was obtained by recrystallization from a mixture of acetone and hexane.

Specific rotation $[\alpha]_D^{25}$=−116.5° (c=0.84, CHCl$_3$). Infrared Absorption Spectrum (KBr), $v_{max}$ cm$^{-1}$: 3200 (broad), 1742. Nuclear Magnetic Resonance Spectrum (CDCl$_3$), δ ppm: 1.17 (3H, doublet, J=7 Hz); 3.46 (2H, singlet); 3.49 (1H, quartet, J=7 Hz); 3.80 (3H, singlet); 4.84 (1H, doublet, J=15 Hz); 5.15 (1H, singlet); 5.18 (1H, doublet, J=15 Hz); 6.5–7.0 (2H, multiplet); 7.1–7.6 (1H, multiplet); 7.73 (1H, singlet); 7.87 (1H, singlet).

EXAMPLE 5

(2R,3R)-3-(Cyanomethylthio)-2-(2,4-difluorophenyl)-1-(1H-1,2,4-triazol-1yl)-2 -butanol and its oxalate

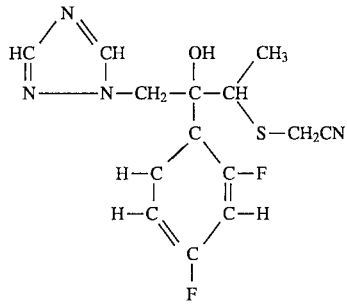

90 mg (1.2 mole) of anhydrous chloroacetonitrile and 112 mg (1.11 mole) of triethylamine were added to a solution of 301 mg (1.05 mole) of (2R,3R)-2-(2,4-difluorophenyl)-3-mercapto-1-(1H- 1,2,4-triazol-1-yl)-2-butanol in 12 ml of anhydrous methylene chloride, and the mixture was stirred at room temperature for 5 hours. At the end of this time, the reaction mixture was partitioned between ethyl acetate and a dilute aqueous solution of sodium carbonate, whilst ice-cooling. The organic layer was washed twice, each time with a saturated aqueous solution of sodium chloride, after which it was dried and then the solvent was removed by distillation under reduced pressure. The crude product thus obtained was purified by column chromatography through silica gel, using a gradient elution method with mixtures of ethyl acetate and hexane ranging from 1:1 to 2:1 by volume as the eluent, to afford 280 mg of the title compound as an oil.

Specific rotation $[\alpha]_D^{25}=-158.5°$ (c=1.11, $CHCl_3$). Infrared Absorption Spectrum ($CHCl_3$), $\nu_{max}$ $cm^{-1}$: 3410, 1620, 1600, 1500. Nuclear Magnetic Resonance Spectrum ($CDCl_3$), δ ppm: 1.23 (3H, doublet, J=7 Hz); 3.48 (1H, quartet, J=7 Hz); 3.58 (2H, singlet); 5.02 (2H, broad singlet); 5.36 (1H, broad singlet); 6.5–7.1 (2H, multiplet); 7.1–7.7 (1H, multiplet); 7.8 (1H, singlet); 7.87 (1H, singlet).

35.9 mg (0.339 mole) of oxalic acid were added to a solution of 110 mg (0.339 mole) of the above compound in 5 ml of ethyl acetate. The residue obtained by distilling off the solvent was recrystallized from a mixture of diethyl ether and hexane, to afford 133 mg of the oxalate of the title compound, melting at 113°–116° C. Specific rotation $[\alpha]_D^{25}=-72.4°$ (c=0.55, methanol).

EXAMPLE 6

(2R,3R)-3-(Cyanomethylsulfonyl)-2-(2,4-difluorophenyl)-1-(1H-1,2,4-triazol-1-yl)- 2-butanol and its nitrate

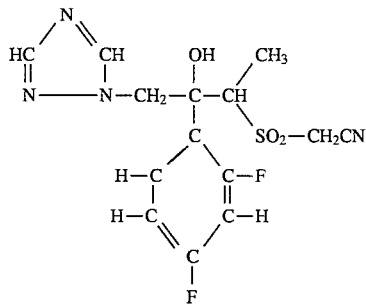

117 mg (0.678 mmole) of 3-chloroperbenzoic acid were added, whilst ice-cooling, to a solution of 86 mg (0.27 mmole) of (2R,3R)-3-(cyanomethylthio)-2-(2,4-difluorophenyl)-1-(1H-1,2,4 -triazol-1-yl)-2-butanol (prepared as described in Example 5) in 2 ml of methylene chloride. The reaction mixture was allowed to warm to room temperature, after which it was stirred for 2 hours and then mixed with an aqueous solution of sodium thiosulfate and a dilute aqueous solution of sodium hydrogencarbonate; it was then extracted with ethyl acetate. The organic extract was washed with a saturated aqueous solution of sodium chloride, and then the solvent was removed by distillation under reduced pressure. The resulting oily residue was purified by column chromatography through silica gel, using a gradient elution method with mixtures of ethyl acetate and hexane ranging from 1:1 to 2:1 by volume as the eluent, to afford 82 mg of the title compound as an oil.

Specific rotation $[\alpha]_D^{25}=-64.8°$ (c=0.52, $CHCl_3$). Infrared Absorption Spectrum ($CHCl_3$), $\nu_{max}$ $cm^{-1}$: 3360, 1620, 1600, 1510. Nuclear Magnetic Resonance Spectrum ($CDCl_3$), δ ppm: 1.37 (3H, doublet, J=7.5 Hz); 3.90 (1H, quartet, J=7.5 Hz); 4.44 (2H, singlet); 4.97 (1H, doublet, J=15 Hz); 5.43 (1H, doublet, J=15 Hz); 6.09 (1H, singlet); 6.5–7.1 (2H, multiplet); 7.1–7.6 (1H, multiplet); 7.81 (1H, singlet); 7.83 (1H, singlet).

0.7 ml of a 2% w/v solution of nitric acid in diethyl ether were added to a solution of 77 mg (0.22 mmole) of the above compound in 3 ml of ethyl acetate. The solid obtained by distilling off the solvent was recrystallized from a mixture of ethyl acetate and benzene, to afford 72 mg of the nitrate of the title compound, melting at 143°–147° C. (with decomposition). Specific rotation $[\alpha]_D^{25}=-29.8°$ (c=0.52, methanol).

EXAMPLE 7

(2R,3R)-2-(4-Chlorophenyl)-3-(cyanomethylthio)-1-(1H-1,2,4l-triazol-1-yl)-2 -butanol and its oxalate

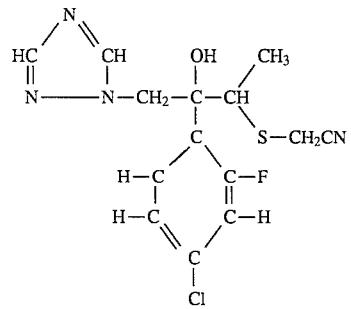

Following a procedure similar to that described in Example 5, but using 80 mg of (2R,3R)-2-(4-chlorophenyl)-3-mercapto-1-(1H-1,2,4 -triazol-1-yl)-2-butanol as a starting material, there were obtained 77 mg of the title compound as an oil.

Specific rotation $[\alpha]_D^{25}=-141°$ (c=0.51, $CHCl_3$). Infrared Absorption Spectrum ($CHCl_3$), $\nu_{max}$ $cm^{-1}$: 3430, 1610, 1508, 1498. Nuclear Magnetic Resonance Spectrum ($CDCl_3$), δ ppm: 1.24 (3H, doublet, J=7 Hz); 3.26 (1H, quartet, J=7 Hz); 3.53 (2H, singlet); 4.58 (1H, doublet, J=14 Hz); 5.02 (1H, doublet, J=14 Hz); 5.13 (1H, broad singlet); 6.23 (4H, singlet); 7.70 (1H, singlet); 7.75 (1H, singlet).

A solution of 71 mg of the title compound in a mixture of ethyl acetate and hexane was mixed with a molar equivalent of oxalic acid and worked up in a conventional way to afford 77 mg of the oxalate of the title compound, melting at 76°–80° C. (with decomposition).

Specific rotation $[\alpha]_D^{25}=-33.1°$ (c=0.51, methanol).

EXAMPLE 8

(2R,3R)-3-(Carbamoylmethylthio)-2-(2,4-difluorophenyl)-1-(1H-1,2,4-triazol-1-yl)- 2-butanol

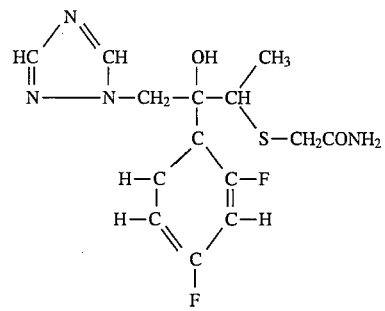

58 mg (0.42 mmole) of 2-bromoacetamide and 48 mg (0.35 mmole) of potassium carbonate were added to a solution of 100 mg (0.35 mmole) of (2R,3R)-2-(2,4-difluorophenyl)-3-mercapto-1-(1H- 1,2,4-triazol-1-yl)-2-butanol in 3 ml of anhydrous dimethylformamide, and the mixture was stirred at room temperature for 1 hour. At the end of this time, the reaction mixture was diluted with benzene and washed with a saturated aqueous solution of sodium chloride, after which the solvent was removed by distillation under reduced pressure. The virtually pure product thus obtained was recrystallized from a mixture of acetone and hexane to afford 90 mg of the title compound, melting at 144°–145° C.

Specific rotation $[\alpha]_D^{25}=-39.9°$ (c=1.03, methanol). Infrared Absorption Spectrum (KBr), $\nu_{max}$ cm$^{-1}$: 3366, 3219, 1658. Nuclear Magnetic Resonance Spectrum (hexadeuterated dimethyl sulfoxide), δ ppm: 1.03 (3H, doublet, J=7 Hz); 3.21 (1H, doublet, J=14.5 Hz); 3.29 (1H, doublet, J=14.5 Hz); 3.60 (1H, quartet, J=7 Hz); 4.74 (1H, doublet, J=14.5 Hz); 4.98 (1H, doublet, J=14.5 Hz); 6.24 (1H, singlet); 6.6–7.0 (1H, multiplet); 7.0–7.5 (3H, multiplet); 7.62 (2H, singlet); 8.27 (1H, singlet).

EXAMPLE 9

(2R,3R)-3-(Carbamoylmethylsulfonyl)-2-(2,4-difluorophenyl)-1-(1H-1,2,4-triazol-1 -yl)-2-butanol

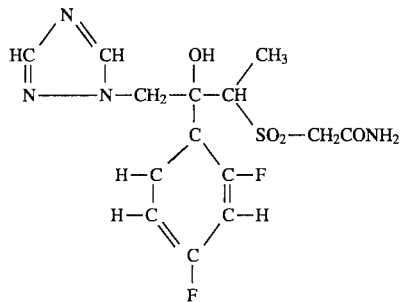

149 mg (0.86 mmole) of 3-chloroperbenzoic acid were added to a solution of 140 mg (0.41 mmole) of (2R,3R)-3-(carbamoylmethylthio)-2-(2,4-difluorophenyl)-1-(1H-1,2,4-triazol-1-yl)- 2-butanol (prepared as described in Example 8) in 30 ml of methylene chloride, and the mixture was stirred overnight at room temperature. At the end of this time, the reaction mixture was washed, in turn, with an aqueous solution of sodium thiosulfate, with a dilute aqueous solution of sodium hydrogencarbonate and with a saturated aqueous solution of sodium chloride, after which the solvent was removed by distillation under reduced pressure. The residual solid was recrystallized from a mixture of methanol and hexane to afford 120 mg of the title compound melting at 184°–185° C.

Specific rotation $[\alpha]_D^{25}=-35.4°$ (c=1.00, dimethylformamide). Infrared Absorption Spectrum (KBr), $\nu_{max}$ cm$^{-1}$: 3367, 3286, 1670. Nuclear Magnetic Resonance Spectrum (hexadeuterated dimethyl sulfoxide+D$_2$O), δ ppm: 1.14 (3H, doublet, J=7 Hz ); 3.39 (2H, singlet); 4.42 (1H, quartet, J=7 Hz ); 4.81 (1H, doublet, J=14.5 Hz); 5.31 (1H, doublet, J=14.5 Hz); 6.4–7.0 (1H, multiplet); 7.0–7.5 (2H, multiplet); 7.64 (1H, singlet); 8.31 (1H, singlet).

EXAMPLE 10

(2R,3R)-2-(2,4-Difluorophenyl)-3-{[(R and S)-2-oxoazetidin-4-yl)thio}-1-(1 H-1,2,4-triazol-1-yl)-2-butanol and its p-toluenesulfonate

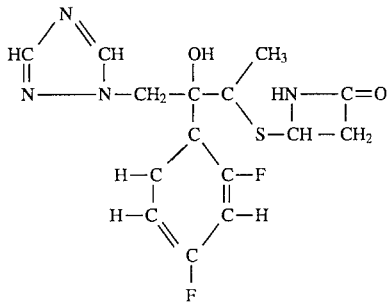

Whilst ice-cooling, 22.5 mg (0.52 mmole) of sodium hydride (as a 55% w/w dispersion in mineral oil) were added to 5 ml of methanol, and subsequently 138 mg (0.48 mmole) of (2R,3R)-2-(2,4-difluorophenyl)-3-mercapto-1-(1H-1,2,4-triazol-1 -yl)-2-butanol and 150 mg (1.16 mole) of 4-acetoxy-2-azetidinone were added to the resulting mixture. The mixture was then stirred for 30 minutes whilst ice-cooling. At the end of this time, the reaction mixture was mixed with water and extracted with ethyl acetate. The extract was washed with a saturated aqueous solution of sodium chloride, after which the solvent was removed by distillation under reduced pressure. The resulting oily residue was then purified by column chromatography through silica gel, using a mixture of ethyl acetate and hexane as the eluent, to afford 150 mg (yield 87%) of the title compound as a foam, consisting of a 1:1 diastereomeric mixture.

Specific rotation $[\alpha]_D^{25}=-26.5°$ (c=1.10, CHCl$_3$). Infrared Absorption Spectrum (CHCl$_3$), $\nu_{max}$ cm$^{-1}$: 3400 (broad), 1760. Nuclear Magnetic Resonance Spectrum (hexadeuterated dimethyl sulfoxide+D$_2$O), δ ppm: 1.23 (1.5H, doublet of doublets, J=7 & 1 Hz); 1.33 (1.5H, doublet, J=7 Hz); 2.89 (0.5H, doublet of doublets, J=15 & 2.4 Hz); 2.94 (0.5H, doublet of doublets, J=15 & 2.4 Hz); 3.37 (0.5H, quartet, J=7 Hz); 3.43 (0.5H, quartet, J=7 Hz ); 3.43 (0.5H, doublet of doublets, J=15 & 5 Hz); 3.49 (0.5H, doublet of doublets, J=15 & 5 Hz); 4.85 (0.5H, doublet of doublets, J=14 & 1 Hz); 4.87 (0.5H, doublet, J=14 Hz); 4.96 (0.5H, doublet of doublets, J=14 & 1 Hz); 5.07 (0.5H, doublet, J=14 Hz); 5.09 (0.5H, doublet of doublets, J=5 & 2.4 Hz); 5.21 (0.5H, doublet of doublets, J=5 & 2.4 Hz); 6.65–6.85 (2H, multiplet); 7.3–7.5 ( 1H, multiplet); 7.78 (0.5H, singlet); 7.80 (0.5H, singlet); 7.82 (0.5H, singlet); 7.84 (0.5H, singlet).

47 mg of p-toluenesulfonic acid (monohydrate) were added to a solution of 87 mg of the above compound in ethyl acetate, and the mixture was then freed from the solvent by distillation. The residue was triturated with diethyl ether to afford 121 mg of the p-toluenesulfonate salt as an amorphous powder.

EXAMPLE 11

(2R,3R)-2-(2,4-Difluorophenyl)-3-[(1,3-dioxolan-2-yl)-methylthio]-1-(1H-1,2,4-triazol-1-yl)-2-butanol and its oxalate

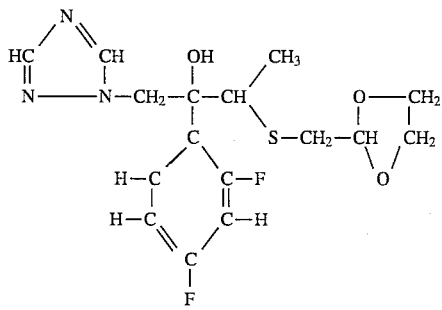

Following a procedure similar to that described in Example 1, but using 193 mg of (2R,3S)-2-(2,4-difluorophenyl)-3-methyl-2-[(1H- 1,2,4-triazol-1-yl)methyl]oxirane and 160 mg of (1,3-dioxolan-2-yl)methanethiol, there were obtained 178 mg of the title compound as an oil.

Specific rotation $[\alpha]_D^{25}=-56°$ (c=0.53, methanol). Nuclear Magnetic Resonance Spectrum (CDCl$_3$), δ ppm: 1.16 (3H, doublet, J=7 Hz); 2.91 (2H, doublet-like, J=5 Hz); 3.57 (1H, quartet, J=7 Hz); 3.8–4.2 (4H, multiplet); 4.87 (1H, doublet, J=14 Hz); 4.95 (1H, singlet); 5.15 (1H, triplet, J=5 Hz); 5.19 (1H, doublet, J=14 Hz); 6.6–7.0 (2H, multiplet); 7.2–7.6 (1H, multiplet); 7.78 (1H, singlet); 7.88 (1H, singlet).

A solution of the above compound in a mixture of ethyl acetate and hexane was mixed with a molar equivalent of oxalic acid and the mixture was worked up in a conventional manner to afford the oxalate of the title compound, melting at 115°–117° C.

EXAMPLE 12

(2R,3R)-3-[(1-Cyanoethyl)thio]-2-(2,4-difluorophenyl)-1-(1H-1,2,4-triazol- 1-yl)-2-butanol

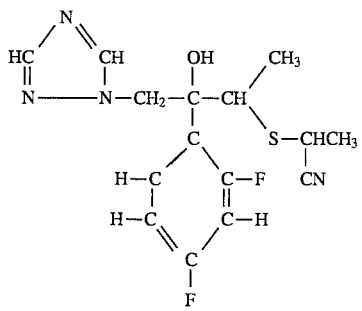

134 mg (1.00 mmole) of 2-bromopropionitrile and 69 mg (0.50 mmole) of potassium carbonate were added to a solution of 143 mg (0.50 mmole) of (2R,3R)-2-(2,4-difluorophenyl)-3-mercapto-1-(1H- 1,2,4-triazol-1-yl)-2-butanol in 3 ml of dimethylformamide, and the resulting mixture was stirred at room temperature for 1 hour under an atmosphere of nitrogen. The reaction mixture was then dissolved in benzene, and the resulting solution was washed, in turn, with water and with a saturated aqueous solution of sodium chloride. The solvent was then removed by distillation under reduced pressure, after which the resulting oily residue was purified by preparative thin layer chromatography on silica gel, using a 3:2 by volume mixture of ethyl acetate and hexane as the developing solvent, to afford 57 mg of stereoisomer A of the title compound (having the lower polarity) as an oil and 72 mg of stereoisomer B of the title compound (having the higher polarity) as crystals; these crystals were recrystallized from a mixture of benzene and hexane to give a pure specimen melting at 66°–68° C.

Stereoisomer A:

Specific rotation $[\alpha]_D^{25}=-192°$ (c=0.97, CHCl$_3$). Infrared Absorption Spectrum (CHCl$_3$), ν$_{max}$ cm$^{-1}$: 3400, 1617, 1498. Nuclear Magnetic Resonance Spectrum (CDCl$_3$), δ ppm: 1.24 (3H, doublet, J=7 Hz); 1.64 (3H, doublet, J=7 Hz); 3.54 (1H, broad quartet, J=7 Hz); 3.90 (1H, quartet, J=7 Hz); 4.90 (1H, doublet, J=14 Hz); 5.10 (1H, doublet, J=14 Hz); 5.26 (1H, singlet); 6.5–7.0 (2H, multiplet); 7.1–7.6 (1H, multiplet); 7.79 (1H, singlet); 7.80 (1H, singlet).

Hexane was added to a solution of 57 mg of this compound and 17 mg of oxalic acid dissolved in 2 ml of ethyl acetate, and the crystals which precipitated were collected by filtration to afford 60 mg of the oxalate of stereoisomer A, melting at 137°–138° C.

Stereoisomer B:

Specific rotation $[\alpha]_D^{25}=-46.0°$ (c=0.83, CHCl$_3$) Infrared Absorption Spectrum (CHCl$_3$), ν$_{max}$ cm$^{-1}$: 3400, 1615, 1498. Nuclear Magnetic Resonance Spectrum (CDCl$_3$), δ ppm: 1.24 (3H, doublet, J=7 Hz); 1.64 (3H, doublet, J=7 Hz); 3.51 (1H, broad quartet, J=7 Hz); 3.93 (1H, quartet, J=7 Hz ); 4.99 (2H, singlet); 5.28 (1H, singlet); 6.5–7.0 (2H, multiplet); 7.1–7.6 (1H, multiplet); 7.76 (1H, singlet); 7.83 (1H, singlet).

EXAMPLE 13

(2R,3R)-3-[(1-Cyanoethyl)sulfinyl]-2-(2,4-difluorophenyl)-1-(1H-1,2,4-triazol- 1-yl)-2-butanol and its nitrate

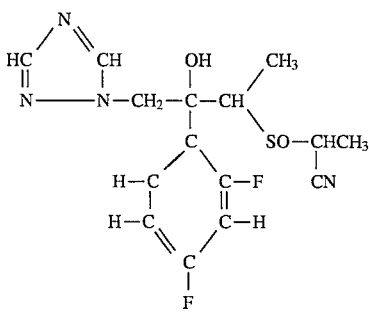

(1) 205 mg (1.19 mmole) of 3-chloroperbenzoic acid were added, whilst ice-cooling and stirring, to a solution of 402 mg (1.19 mmole) of isomer A of (2R,3R)-3-[(1-cyanoethyl)thio]-2-(2,4-difluorophenyl)-1-(1H-1,2,4-triazol-1 -yl)-2-butanol (prepared as described in Example 12) in 15 ml of methylene chloride, and the resulting mixture was stirred at the same temperature for 30 minutes. At the end of this time, the reaction mixture was washed with a 5% w/v aqueous solution of sodium thiosulfate and with a 3% aqueous solution of sodium hydrogencarbonate, in that order, and the solvent was removed by distillation under reduced pressure. The resulting oily residue was then purified by column chromatography through 15 g of silica gel, using a 4:1 by volume mixture of ethyl acetate and hexane as the eluent, to afford 381 mg of the title compound as an oil. The product was a mixture of two diastereomers, the separation of which was carried out by passing it through a Lobar column, using ethyl acetate as the eluent, to afford 220 mg of a pure isomer with the higher polarity as an oil.

Infrared Absorption Spectrum (CHCl$_3$), $v_{max}$ cm$^{-1}$: 3390, 2250, 1615, 1500. Nuclear Magnetic Resonance Spectrum (CDCl$_3$), δ ppm: 1.13 (3H, doublet, J=7 Hz); 1.74 (3H, doublet, J=7 Hz); 3.69 (1H, quartet, J=7 Hz); 3.76 (1H, quartet, J=7 Hz); 4.91 (2H, singlet); 5.78 (1H, singlet); 6.5–7.1 (2H, multiplet); 7.1–7.7 (1H, multiplet); 7.80 (1H, singlet); 7.92 (1H, singlet).

A 5% w/v aqueous solution of nitric acid (one molar equivalent) in diethyl ether was added to a solution of the above compound dissolved in diethyl ether, to give the nitrate of the title compound as crystals, melting at 140°–142° C.

(2) In a similar manner to the procedure described above, 570 mg of isomer B of (2R,3R)-3-[(1-cyanoethyl)thio]-2-(2,4-difluorophenyl)-1-( 1H-1,2,4-triazol-1-yl)-2-butanol (prepared as described in Example 12) were oxidized with one molar equivalent of 3-chloroperbenzoic acid, and the crude product was purified by column chromatography through silica gel. There were obtained 521 mg of the title compound as an oily mixture of two diastereomers, the separation of which was carried out by chromatography using a Lobar column to afford 228 mg of a pure isomer with the higher polarity as an oil.

Infrared Absorption Spectrum (CHCl$_3$), $v_{max}$ cm$^{-1}$: 3400, 2255, 1620, 1505. Nuclear Magnetic Resonance Spectrum (CDCl$_3$) δ ppm: 1.11 (3H, doublet, J=7 Hz); 1.65 (3H, doublet, J=7 Hz); 3.72 (1H, quartet, J=7 Hz); 3.78 (1H, quartet, J=7 Hz); 4.89 (2H, singlet); 5.87 (1H, singlet); 6.5–7.1 (2H, multiplet); 7.1–7.7 (1H, multiplet); 7.80 (1H, singlet); 7.97 (1H, singlet).

A 5% w/v aqueous solution of nitric acid (one molar equivalent) in diethyl ether was added to a solution of the above compound dissolved in diethyl ether, to give the nitrate of the title compound as a crystals, melting at 128°–131° C.

EXAMPLE 14

(2R,3R)-2-(2,4-Difluorophenyl)-3-(methoxymethylthio)-1l-(1H-1,2,4-triazol-1-yl)-2-butanol

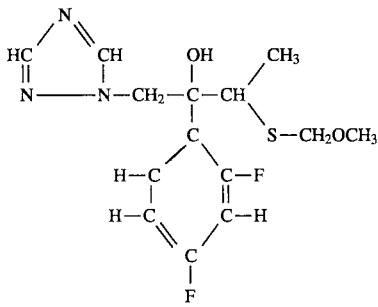

215 mg (2.67 mmole) of methoxymethyl chloride, followed by 217 mg (1.68 mole) of diisopropylethylamine, were added to a solution of 400 mg (1.40 mole) of (2R,3R)-2-(2,4-difluorophenyl)-3-mercapto-1-(1H-1,2,4-triazol-1-yl)-2 -butanol in 10 ml of methylene chloride, at 0° C. with stirring, and the resulting mixture was then stirred at the same temperature for 15 minutes, after which it was allowed to stand at room temperature for 30 minutes. At the end of this time, the reaction mixture was mixed with a dilute aqueous solution of sodium hydrogencarbonate and extracted with ethyl acetate. The extract was dried and then concentrated by distilling off the solvent under reduced pressure. The resulting crystalline residue was then recrystallized from a mixture of ethyl acetate and hexane, to afford 235 mg of the title compound melting at 110°–112° C.

Specific rotation $[\alpha]_D^{25}$=–55° (c=0.59, CHCl$_3$). Infrared Absorption Spectrum (KBr), $v_{max}$ cm$^{-1}$: 3186 (broad), 1615, 1499. Nuclear Magnetic Resonance Spectrum (CDCl$_3$) δ ppm: 1.18 (3H, doublet, J=7 Hz); 3.50 (3H, singlet); 3.59 ( 1H, quartet, J=7 Hz); 4.63 (1H, doublet, J=12 Hz); 4.83 (1H, doublet, J=14 Hz); 4.84 (1H, doublet, J=14 Hz); 4.88 (1H, singlet); 6.5–7.0 (2H, multiplet); 7.2–7.6 (1H, multiplet); 7.75 (1H, singlet); 7.89 (1H, singlet).

EXAMPLE 15

(2R,3R)-2-(2,4-Difluorophenyl)-3-(methoxymethylsulfonyl)-1-(1H-1,2,4-triazol-1-yl)-2-butanol

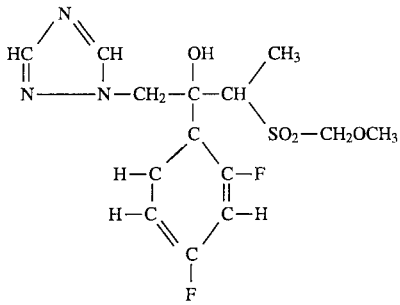

280 mg (1.62 mmole) of 3-chloroperbenzoic acid were added, whilst ice-cooling and stirring, to a solution of 190 mg (0.58 mmole) of (2R,3R)-2-(2,4-difluorophenyl)-3-(methoxymethylthio)-1-(1H- 2,4-triazol-1-yl)-2-butanol (prepared as described in Example 14) in 7 ml of methylene chloride, and the resulting mixture was kept at the same temperature for 5 minutes, after which it was stirred at room temperature for 1 hour. At the end of this time, the reaction mixture was mixed with an aqueous solution of sodium sulfite and then with a dilute aqueous solution of sodium hydrogencarbonate, and extracted with ethyl acetate. The extract was then dried and concentrated by distilling off the solvent. The resulting crude residue was purified by column chromatography through silica gel, using a 1:1 by volume mixture of ethyl acetate and hexane as the eluent, to afford 171 mg of the title compound as a solid. A pure specimen, melting at 102°–103° C., was obtained by recrystallization of this solid from a mixture of benzene and hexane.

Specific rotation $[\alpha]_D^{25}$=–108° (c=0.51, CHCl$_3$). Infrared Absorption Spectrum (KBr), $v_{max}$ cm$^{-1}$: 3439, 1617, 1505. Nuclear Magnetic Resonance Spectrum (CDCl$_3$), δ ppm: 1.26 (3H, doublet, J=7 Hz); 3.77 (3H, singlet); 3.81 (1H, quartet, J=7 Hz); 4.50 (1H, doublet, J=12 Hz); 4.97 (1H, doublet, J=12 Hz); 4.99 (1H, doublet, J=15 Hz); 5.43 (1H, singlet); 5.49 (1H, singlet); 6.5–7.0 (2H, multiplet); 7.1–7.6 (1H, multiplet); 7.77 (1H, singlet); 7.86 (1H, singlet).

EXAMPLE 16

(2R,3R)-2-(4-Chlorophenyl)-3-(methoxymethylthio)-1-(1H-1,2,4-triazol-1-yl)-2-butanol

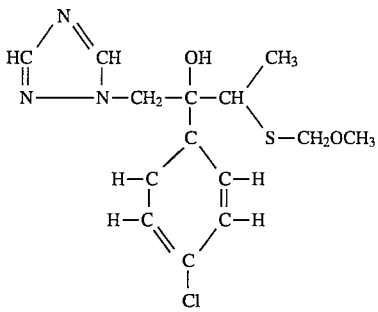

Following a procedure similar to that described in Example 14, but using 360 mg of (2R,3R)-2-(4-chlorophenyl)-3-mercapto-1-(1H-1,2,4-triazol-1-yl)-2-butanol as a starting material, 220 mg of the title compound were obtained as a solid after purification by column chromatography through silica gel and using a 2:1 by volume mixture of ethyl acetate and hexane as the eluent. A pure specimen, melting at 122° C., was obtained by recrystallization from a mixture of ethyl acetate and hexane.

Specific rotation $[\alpha]_D^{25} = -12.0°$ (c=0.50, CHCl$_3$). Nuclear Magnetic Resonance Spectrum (CDCl$_3$), δ ppm: 1.20 (3H, doublet, J=7 Hz); 3.31 (1H, quartet, J=7 Hz); 3.47 (3H, singlet); 4.55 (1H, doublet, J=12 Hz); 4.58 (1H, doublet, J=14 Hz); 4.76 (1H, singlet); 4.81 (1H, doublet, J=12 Hz); 4.90 (1H, doublet, J=14 Hz); 7.25 (4H, singlet); 7.82 (2H, singlet).

EXAMPLE 17

(2R,3R)-2-(4-Chlorophenyl)-3-[(1-methoxyethyl)thio]-1-(1H-1,2,4-triazol-1-yl)-2-butanol and its oxalate

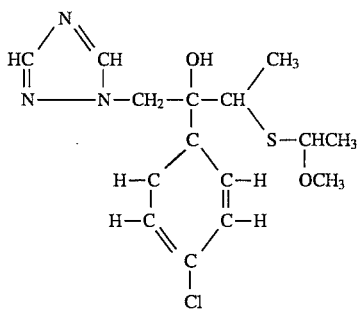

267 mg (2.82 mmole) of 1-methoxyethyl chloride, followed by 219 mg (1.69 mmole) of diisopropylethylamine, were added at 0° C., with stirring, to a solution of 401 mg (1.41 mmole) of (2R,3R)-2-(4-chlorophenyl)-3-mercapto-1-(1H-1,2,4-triazol-1-yl)-2-butanol (prepared as described in Japanese Patent Application No. Hei 2-35928) in 8 ml of methylene chloride. The cooling bath was then removed and the resulting mixture was stirred at room temperature for 1 hour. At the end of this time, the reaction mixture was mixed with a dilute aqueous solution of sodium hydrogencarbonate and extracted with ethyl acetate. The extract was dried and concentrated by distilling off the solvent under reduced pressure. The resulting oily residue was purified by column chromatography through silica gel, using a 2:1 by volume mixture of ethyl acetate and hexane as the eluent, to afford 245 mg of the title compound as an oil. The product was a 1:1 mixture of two diastereomers.

Infrared Absorption Spectrum (CHCl$_3$), $v_{max}$ cm$^{-1}$: 3350, 1515, 1495. Nuclear Magnetic Resonance Spectrum (CDCl$_3$), δ ppm: 1.20, 1.26 (3H, doublet, J=7 Hz); 1.47, 1.50 (3H, doublet, J=6 Hz); 3.30, 3.38 (3H, singlet); 3.13, 3.32 (1H, quartet, J=7 Hz); 4.47, 4.54 (1H, doublet, J=14 Hz); 4.80 (1H, quartet, J=6 Hz); 4.88, 5.02 (together 1H, each doublet, J=14 Hz); 5.00, 5.05 (together 1H, each singlet); 7.00–7.55 (4H, multiplet); 7.75, 7.79 (together 1H, each singlet); 7.83, 7.96 (together 1H, each singlet).

One molar equivalent of oxalic acid was added to a solution of 155 mg of the above compound in ethyl acetate, and the crystals which precipitated on adding hexane were collected by filtration, to give 180 mg of the oxalate of the title compound, melting at 147.5°–149° C.

EXAMPLE 18

(2R,3R)-2-(2,4-Difluorophenyl)-3-(methylthiomethylthio)-1-(1H-1,2,4-triazol-1-yl)-2-butanol

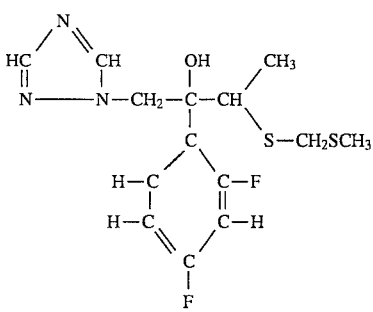

31 mg (0.70 mmole) of sodium hydride (as a 55% w/w dispersion in mineral oil) were washed with anhydrous hexane and then suspended in 2 ml of dimethylformamide. 100 mg (0.35 mmole) of (2R,3R)-2-(2,4-difluorophenyl)-3-mercapto-1-(1H-1,2,4-triazol-1-yl)-2-butanol were then added at 0° C., with stirring, to the resulting suspension. After evolution of hydrogen gas had ceased, 67 mg (0.70 mmole) of methylthiomethyl chloride were added to the mixture. The resulting mixture was then stirred at the same temperature for 1 hour. At the end of this time, the reaction mixture was partitioned between ethyl acetate and an aqueous solution of sodium chloride. The organic layer was dried and concentrated by distilling off the solvent. The crude product thus obtained was purified by column chromatography through silica gel, using a 3:1 by volume mixture of ethyl acetate and hexane as the eluent, to afford 105 mg of the title compound as a solid. A pule specimen (78 mg), melting at 108°–109° C., was obtained by recrystallization of this solid from a mixture of ethyl acetate and hexane.

Specific rotation $[\alpha]_D^{25} = -240°$ (c=0.84, CHCl$_3$). Nuclear Magnetic Resonance Spectrum (CDCl$_3$), δ ppm: 1.17 (3H, doublet, J=7 Hz); 2.25 (3H, singlet); 3.63 (1H, broad quartet, J=7 Hz); 3.77 (2H, singlet); 4.85 (1H, doublet, J=14 Hz); 5.08 (1H, doublet, J=14 Hz); 8.6–7.0 (2H, multiplet); 7.2–7.6 (1H, multiplet); 7.76 (1H, singlet); 7.82 (1H, singlet).

EXAMPLE 19

(2R,3R)-2-(4-Chlorophenyl)-3-(methylthiomethylthio)-1-(1H-1,2,4-triazol-1-yl)-2-butanol

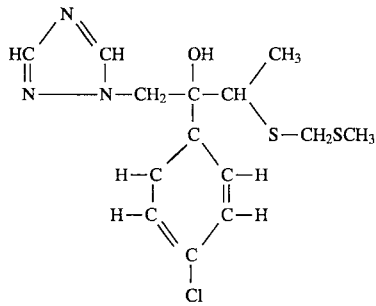

Following a procedure similar to that described in Example 17, but using 150 mg of (2R,3R)-2-(4-chlorophenyl)-3-mercapto-1-(1H-1,2,4 -triazol-1-yl)-2-butanol as a starting material, there were obtained 138 mg of the title compound, melting at 163°–163.5° C., after recrystallization from a mixture of ethyl acetate and hexane.

Specific rotation $[\alpha]_D^{25}=-217°$ (c=1.05, CHCl$_3$). Infrared Absorption Spectrum (KBr), $\nu_{max}$ cm$^{-1}$: 3184, 1511, 1492. Nuclear Magnetic Resonance Spectrum (CDCl$_3$), δ ppm: 1.20 (3H, doublet, J=7 Hz); 2.20 (3H, singlet); 3.32 (1H, quartet, J=7 Hz); 3.71 (2H, singlet); 4.55 (1H, doublet, J=14 Hz); 4.56 (1H, singlet); 5.05 (1H, doublet, J=14 Hz); 7.10–7.45 (4H, multiplet); 7.76 (1H, singlet); 7.83 (1H, singlet).

EXAMPLE 20

(2R,3R)-3-(Cyanomethylsulfinyl)-2-(2,4-difluorophenyl)-1-(1H-1,2,4-triazol-1-yl)- 2-butanol

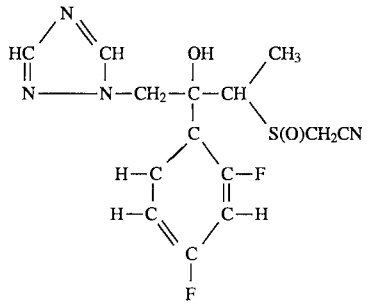

205 mg (1.19 mole) of 3-chloroperbenzoic acid were added, whilst ice-cooling and stirring, to a solution of 350 mg (1.08 mole) of (2R,3R)-3-(cyanomethylthio)-2-(2,4-difluorophenyl)-1-(1H- 1,2,4-triazol-1-yl)-2butanol (prepared as described in Example 5) in 7 ml of methylene chloride, and the resulting mixture was stirred at the same temperature for 20 minutes. At the end of this time, the reaction mixture was partitioned between ethyl acetate and an aqueous solution of sodium sulfite. The organic layer was collected and washed with a dilute aqueous solution of sodium hydrogencarbonate and with a saturated aqueous solution of sodium chloride, in that order, and the solvent was removed by distillation under reduced pressure. The resulting residue was then purified by column chromatography through 10 g of silica gel. Elution with a 4:1 by volume mixture of ethyl acetate and benzene gave 113 mg of one isomer of the title compound with the lower polarity as a crystalline mass, which was recrystallized from a mixture of ethyl acetate and hexane to afford a pure specimen melting at 138°–140° C.

Specific rotation $[\alpha]_D^{25}=-156°$ (c=0.53, CHCl$_3$). Infrared Absorption Spectrum (KBr), $\nu_{max}$ cm$^{-1}$: 3505, 2250, 1618, 1598, 1504. Nuclear Magnetic Resonance Spectrum (CDCl$_3$), δ ppm: 1.06 (3H, doublet, J=7 Hz); 3.64 (1H, doublet, J=16.5 Hz); 3.77 (1H, quartet, J=7 Hz); 4.08 (1H, doublet, J=16.5 Hz); 4.98 (1H, doublet, J=14 Hz); 5.22 (1H, doublet, J=14 Hz); 5.82 (1H, singlet); 6.7–6.9 (2H, multiplet); 7.2–7.4 (1H, multiplet); 7.78 (1H, singlet); 7.81 (1H, singlet).

Further elution with 5% v/v methanol-ethyl acetate gave 169 mg of another isomer of the title compound with the higher polarity as a crystalline mass, which was recrystallized from a mixture of acetone and diisopropyl ether to afford a pure specimen melting at 80°–84° C.

Specific rotation $[\alpha]_D^{25}=-139°$ (c=0.55, CHCl$_3$). Infrared Absorption Spectrum (KBr), $\nu_{max}$ cm$^{-1}$: 3260, 2250, 1618, 1598, 1520. Nuclear Magnetic Resonance Spectrum (CDCl$_3$), δ ppm: 1.22 (3H, doublet, J=7 Hz); 3.74 (1H, quartet, J=7 Hz); 3.90 (2H, singlet); 4.83 (1H, doublet, J=14 Hz); 5.06 (1H, doublet, J=14 HZ); 5.76 (1H, singlet); 6.6–6.9 (2H, multiplet); 7.4–7.5 (1H, multiplet); 7.83 (1H, singlet); 7.92 (1H, singlet).

EXAMPLE 21

(2R,3R)-2-(2,4-Difluorophenyl)-3-(tetrahydrofuran-3-ylthio)-1-(1H-1,2,4-triazol- 1-yl)-2-butanol and its oxalate

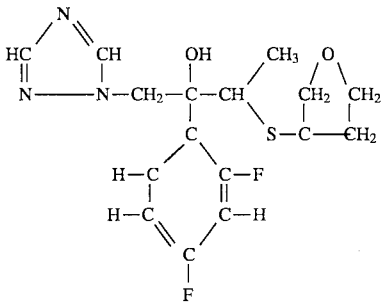

20 mg (0.46 mmole) of sodium hydride (as a 55% w/w dispersion in mineral oil) were washed with hexane, and then suspended in 1.5 ml of dimethylformamide. 130 mg (0.46 mole) of (2R,3R)-2-(2,4-difluorophenyl)-3-mercapto1-(1H-1,2,4-triazol-1 -yl)-2-butanol were added to the resulting suspension under an atmosphere of nitrogen, whilst ice-cooling, and the mixture was stirred for 10 minutes. At the end of this time, 92 mg (0.55 mole) of (±)-3-(methanesulfonyloxy)tetrahydrofuran were added to the mixture, and the resulting mixture was stirred at 60°–65° C. for 2 hours. After this time, the mixture was cooled, after which it was diluted with ethyl acetate. The mixture was then washed with a saturated aqueous solution of sodium chloride. The solvent was removed by distillation under reduced pressure. The crude product thus obtained was chromatographed through 15 g of silica gel, using a 2:1 by volume mixture of ethyl acetate and hexane as the eluent, to afford 139 mg of a mixture of the title compound and an unidentified byproduct as an oil, the separation of which was carried out by passing it through a Lobar column, using ethyl acetate, to yield 85 mg of a pure specimen of the title compound as an oil.

Infrared Absorption Spectrum (CHCl$_3$), $v_{max}$ cm$^{-1}$: 3425, 1615, 1595. Nuclear Magnetic Resonance Spectrum (CDCl$_3$), δ ppm: 1.15 (3H, doublet, J=7 Hz); 1.57–2.65 (2H, multiplet); 3.33 ( 1H, quartet, J=7 Hz); 3.4–4.5 (5H, multiplet); 4.82 (1H, doublet, J=15 Hz); 4.94 (1H, singlet); 5.14 (1H, doublet, J=15 Hz); 6.4–7.1 (2H, multiplet); 7.1–7.7 (1H, multiplet); 7.76 (1H, singlet); 7.87 (1H, singlet).

One molar equivalent of oxalic acid was added to a solution of 73 mg of the above compound in ethyl acetate, and the crystals that precipitated on adding hexane were collected by filtration, to give 56 mg of the oxalate of the title compound melting at 162°–164° C.

EXPERIMENT

Anti-fungal Activity

Groups of mice (each group containing 10 mice) were inoculated with between 7 and 9×10$^6$ spores per mouse of *Candida albicans*. 1, 4 and 24 hours after the inoculation, 20 mg/kg of the test compound was orally administered each time to each mouse. The anti-fungal activity was assessed by the survival rate 9 days after infection. The survival rate was recorded as 0% 2 days after infection in an untreated (control) group.

TABLE 2

| Compound | Survival rate (%) |
|---|---|
| Example 3 | 100 |
| Example 5 | 100 |
| Example 8 | 100 |
| Example 10 | 100 |
| Example 12 (Isomer A) | 100 |
| Example 12 (Isomer B) | 100 |
| Example 13(1) | 100 |
| Example 14 | 100 |
| Example 15 | 100 |
| Example 16 | 100 |
| Example 17 | 100 |
| Example 18 | 100 |
| Ketoconazole | 50 |

As can be seen from the test results given above, the compounds of the present invention exhibit anti-fungal activities which are far better than those of the known compound, ketoconazole, which was used for purposes of comparison.

We claim:

1. A compound selected from the group consisting of 2-(4-chlorophenyl)-3-[(3-thietanyl)-sulfinyl]-1-( 1H-1,2,4-triazol-1-yl)-2-butanol, 2-(2,4-dichlorophenyl)-3-[(3-oxetanyl)-thio]-1-(1H,1,2,4-triazol-1-yl)-2-butanol, 2-(2,4-difluorophenyl)-3-[(3-thietanyl)-thio]-(1H-1,2,4-triazol-1-yl)-2-butanol, 2-(2,4-difluorophenyl)-3-[(S-oxothietan-3-yl)thio]-1-(1H-1,2,4-triazol-1-yl)-2-butanol, 2-(2,4-difluorophenyl)-3-[(S,S-dioxo-thietan-3-yl)thiol]-1-(1H-1, 2,4-triazol-1-yl)-2 -butanol, 2-(2,4-difluorophenyl)-3-(oxetan-3-ylthio)-1-(1H-1,2,4-triazol-1-yl)-2-butanol, and pharmaceutically acceptable salts thereof.

2. The compound of claim 1, selected from the group consisting of 2-(4-chlorophenyl)-3-[(3-thietanyl)sulfinyl]-1-(1H-1,2,4-triazol-1-yl)- 2-butanol and pharmaceutically acceptable salts thereof.

3. The compound of claim 1, selected from the group consisting of 2-(2,4-dichlorophenyl)-3-[(3-oxetanyl)thio]-1-(1H-1,2,4-triazol-1-yl)- 2-butanol and pharmaceutically acceptable salts thereof.

4. The compound of claim 1, selected from the group consisting of 2-(2,4-difluorophenyl)-3-[(3-thietanyl)thio]-1-(1H-1,2,4-triazol-1-yl)- 2-butanol and pharmaceutically acceptable salts thereof.

5. The compound of claim 1, selected from the group consisting of 2-(2,4-difluorophenyl)-3-[(S-oxothietan-3-yl)thio]-1-(1H-1,2,4-triazol-1 -yl)-2-butanol and pharmaceutically acceptable salts thereof.

6. The compound of claim 1, selected from the group consisting of 2-(2,4-difluorophenyl)-3-[(S,S-dioxothietan-3-yl)thio]-1-(1H-1,2,4-triazol- 1-yl)-2-butanol and pharmaceutically acceptable salts thereof.

7. The compound of claim 1, selected from the group consisting of 2-(2,4-difluorophenyl)-3-(oxetan-3-ylthio)-1-(1H-1,2,4-triazol-1-yl)-2 -butanol and pharmaceutically acceptable salts thereof.

8. A pharmaceutical or veterinary composition for the treatment or prophylaxis of fungal infections, which comprises an effective anti-fungal amount of an anti-fungal agent in admixture with a pharmaceutically or veterinarily acceptable carrier or diluent, wherein the anti-fungal agent is at least one compound selected from the group consisting of the compounds of claim 1 or pharmaceutically acceptable salts thereof.

9. A method for the treatment or prophylaxis of fungal infections in an animal, which method comprises administering to said animal an effective anti-fungal amount of an anti-fungal agent, wherein the anti-fungal agent comprises at least one compound selected from the group consisting of compounds of claim 1 or pharmaceutically acceptable salts thereof.

* * * * *

UNITED STATES PATENT AND TRADEMARK OFFICE
CERTIFICATE OF CORRECTION

PATENT NO. : 5,489,606

DATED : February 6, 1996

INVENTOR(S) : OIDA et al

It is certified that error appears in the above-identified patent and that said Letters Patent is hereby corrected as shown below:

Title Page, Left Column, under U.S. PATENT DOCUMENTS, after "5,004,494  4/1991" rewrite "Sugauanam et al" as --Sugavanam et al--.

Title Page, Right Column, after "5,405,861...268.6" insert

--4,507,484   3/1985   Gymer et al....514/383

FOREIGN PATENT DOCUMENTS
  0 061 835   10/1992   Europe
  0 178 533    3/1986   Europe--.

Title Page, Right Column, [57] ABSTRACT, in the first line following the structural formula, after "phenyl;" delete "is"; in the following line, after "cycloalkyl", delete "$R^2$".

Signed and Sealed this

Twenty-fourth Day of November, 1998

Attest:

BRUCE LEHMAN

*Attesting Officer*    Commissioner of Patents and Trademarks